(12) United States Patent
Nishino et al.

(10) Patent No.: US 8,158,587 B2
(45) Date of Patent: Apr. 17, 2012

(54) COMPOUND HAVING HISTONE DEACETYLASE-INHIBITING ACTIVITY, AND PHARMACEUTICAL COMPOSITION COMPRISING THE COMPOUND AS AN ACTIVE INGREDIENT

(75) Inventors: Norikazu Nishino, Fukuoka (JP); Minoru Yoshida, Saitama (JP); Junichi Nakagawa, Hokkaido (JP)

(73) Assignees: Kyushu Institute of Technology, Fukuoka (JP); Riken, Saitama (JP)

( * ) Notice: Subject to any disclaimer, the term of this patent is extended or adjusted under 35 U.S.C. 154(b) by 459 days.

(21) Appl. No.: 12/440,180

(22) PCT Filed: Jul. 30, 2007

(86) PCT No.: PCT/JP2007/064873
§ 371 (c)(1),
(2), (4) Date: Apr. 27, 2009

(87) PCT Pub. No.: WO2008/029565
PCT Pub. Date: Mar. 13, 2008

(65) Prior Publication Data
US 2009/0275728 A1    Nov. 5, 2009

(30) Foreign Application Priority Data

Sep. 5, 2006  (JP) ................................. 2006-239901

(51) Int. Cl.
    A61K 38/12       (2006.01)
(52) U.S. Cl. ...................................... 514/21.1
(58) Field of Classification Search .................... None
    See application file for complete search history.

(56) References Cited

FOREIGN PATENT DOCUMENTS

| JP | 2000-256397 A | 9/2000 |
|---|---|---|
| JP | 2002-527449 A | 8/2002 |
| JP | 2003-505417 A | 2/2003 |
| JP | 3494624 B2 | 2/2004 |
| JP | 2005-517683 A | 6/2005 |
| WO | 99/11659 A1 | 3/1999 |
| WO | 00/21979 A2 | 4/2000 |
| WO | 01/07042 A1 | 2/2001 |
| WO | 03/057722 A | 7/2003 |
| WO | 03/070754 A1 | 8/2003 |
| WO | 2004/113366 A1 | 12/2004 |

OTHER PUBLICATIONS

Hidenori Nakajima et al., "FR901228, a Potent Antitumor Antibiotic, Is a Novel Histone Deacetylase Inhibitor", Experimental Cell Research, 1998, pp. 126-133, vol. 241.
Akiko Saito et al., "A synthetic inhibitor of histone deacetylase, MS-27-275, with marked in vivo autitumor activity against human tumors", Proc. Natl. Acad. Sci. USA, 1999, pp. 4592-4597, vol. 96.
Martin Gottlicher et al., "Valproic acid defines a novel class of HDAC inhibitors inducing differentiation of transformed cells" The EMBO Journal, 2001, pp. 6969-6978, vol. 20, No. 24.
Akihiro Ito et al., "p300/CBP-mediated p53 acetylation is commonly induced by p53-activating agents and inhibited by MDM2", The EMBO Journal, 2001, pp. 1331-1340, vol. 20, No. 6.
Li-Jung Juan et al., "Histone Deacetylases Specifically Down-regulate p53-dependent Gene Activation", The Journal of Biological Chemistry, 2000, pp. 20436-20443, vol. 275, No. 27.
Philippe Dhordain et al., "Corepressor SMRT binds the BTB/POZ repressing domain of the LAZ3/BCL6 oncoprotein", Proc. Natl. Acad. Sci. USA, Sep. 1997, pp. 10762-10767, vol. 94.
Timothy A. McKinsey et al., "Signal-dependent nuclear export of a histone deacetylase regulates muscle differentiation", Nature, Nov. 2, 2000, pp. 106-111, vol. 408.
Ryohei Furumai et al., "FK228 (Depsipeptide) as a Natural Prodrug That Inhibits Class I Histone Deacetylases", Cancer Research, Sep. 1, 2002, pp. 4916-4921, vol. 62.
Mohammed P.I. Bhuiyan et al., "Chlamydocin analogs bearing carbonyl group as possible ligand toward zinc atom in histone deacetylases", Bioorganic & Medicinal Chemistry, 2006, pp. 3438-3446, vol. 14.

(Continued)

Primary Examiner — Christina Bradley
(74) Attorney, Agent, or Firm — Sughrue Mion, PLLC

(57) ABSTRACT

A novel compound having histone deacetylase-inhibiting activity which is a cyclic tetrapeptide derivative represented by the general formula (1) given below and a pharmaceutical composition comprising such compound as an active ingredient. (In the formula, the cyclic tetrapeptide moiety has a known structure; $R_1$ and $R_2$ each independently represents an alkylene group containing 1 to 6 carbon atoms, which may be branched; X represents a group or bond selected from among —CO—, —O—, —S— or —SO—; Y represents a hydrogen or halogen atom, a phenyl group (including a substituted form), a pyridyl group (including a substituted form), an alkyl group (including a halogen-substituted form; hereinafter the same shall apply) containing 1 to 6 carbon atoms, an alkyloxy group containing 1 to 6 carbon atoms, an alkylcarbonyl group containing 1 to 6 carbon atoms, an alkyloxycarbonyl group containing 1 to 6 carbon atoms, an alkylthio group containing 1 to 6 carbon atoms, an alkylthiocarbonyl group containing 1 to 6 carbon atoms or a mono- or dialkylamino group containing 1 to 6 carbon atoms; when Y is a phenyl group (including a substituted form) or a pyridyl group (including a substituted form), it may form a further cyclic structure bound to $R_2$.)

(1)

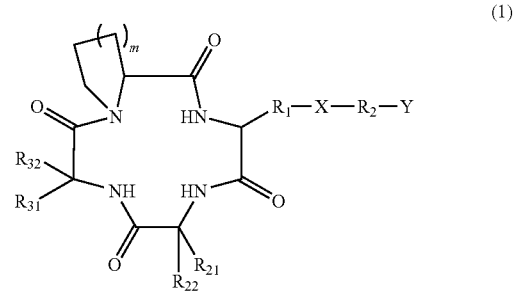

6 Claims, 6 Drawing Sheets

OTHER PUBLICATIONS

Richard E. Shute et al., "Analogues of the Cytostatic and Antimitogenic Agents Chlamydocin and HC-Toxin: Synthesis and Biological Activity of Chloromethyl Ketone and Diazomethyl Ketone Functionalized Cyclic Tetrapeptides", J. Med. Chem., 1987, pp. 71-78, vol. 30.

Yoshinori Hirashima et al., "Design and Synthesis of Histone Deacetylase Inhibitors Containing Trifluoromethylketone Moiety as the Functional Group", Peptide Science, 2005, pp. 141-144.

Poland Gdansk, Journal of Peptides Science, 29th European Peptide Symposium, Sep. 3-8, 2006, Supplement to vol. 12.

Hirashima, et al., Design and synthesis of histone deacetylase inhibitors containing thioether moiety as the functional group; J. Pept. Sci., vol. 12, Issue S1, p. 213 (Aug. 2006).

COMPOUND HAVING HISTONE DEACETYLASE-INHIBITING ACTIVITY, AND PHARMACEUTICAL COMPOSITION COMPRISING THE COMPOUND AS AN ACTIVE INGREDIENT

CROSS REFERENCE TO RELATED APPLICATIONS

This application is a National Stage of International Application No. PCT/JP2007/064873 filed Jul. 30, 2007, claiming priority based on Japanese Patent Application No. 2006-239901, filed Sep. 5, 2006, the contents of all of which are incorporated herein by reference in their entirety.

TECHNICAL FIELD

The present invention relates to a compound having histone deacetylase-inhibiting activity, which is a novel cyclic tetrapeptide derivative, and to a pharmaceutical composition comprising the compound as an active ingredient.

BACKGROUND ART

It is known that chromatin, which is a complex containing DNA and proteins, is present in most eukaryotic cells, and histones (proteins), which are the structural proteins of chromatin, play an important role in gene expression. DNA is entangled with histones to form a chromatin structure and it is said that acetylation of the histone tail of these histones causes a change in chromatin structure (as a result, resulting in gene expression regulation).

More specifically, chromatin is formed by higher order structure formation from a fundamental unit, the so-called nucleosome structure, formed by gene DNA winding around a core histone octamer resulting from association of two molecules each of four kinds of histones. The core histone has a tail-like form in the vicinity of the N terminus thereof which is rich in basic amino acids and has a structure further covering the DNA on the nucleosome. A lysine residue in the vicinity of this tail region is under turnover involving reversible acetylation and is said to be closely involved in structural regulation of the nucleosome itself or in transcriptional control via controlled binding thereof to other proteins (transcription factors, silencer proteins, RNA polymerase, etc.) interacting with the gene DNA.

As a proof of histone acetylation-dependent gene expression control, it is reported that a high degree of histone acetylation promotes the induction of expression from the gene occurring in that region and, on the contrary, deacetylation thereof results in the formation of a transcription-inert region called heterochromatin. Thus, in spite of the fact that histones, which are structural proteins of chromatin, and acetylation thereof extend to all parts of the chromosomal gene, it is suggested that the function thereof exerts a great influence on the expression of certain specific genes and thus is involved in strict control of the so-called nuclear signal transduction. The enzyme effecting the acetylation of histones is histone acetyltransferase and the enzyme effecting deacetylation is histone deacetylase (HDAC) and these enzymes both control the dynamic turnover with respect to the level of histone acetylation.

When the action of histone deacetylase is enhanced, the adequate differentiation of cells or morphological normalization thereof is inhibited; when the enzyme activity of this histone deacetylase is inhibited, the deacetylation of histones is inhibited and, as a result, a high level of histone acetylation is induced and the expression of genes necessary for differentiation and morphological normalization is induced. This phenomenon has been confirmed by studies using trichostatin A and trapoxin analogs, which are histone deacetylase inhibitors (HDAC inhibitors); more specifically, trichostatin A is known to induce the differentiation of leukemia cells, nerve cells, breast cancer cells and so forth. In addition, when these inhibitors are caused to act on cells at still higher concentration levels, the protein p21 inhibiting the cyclin-dependent protein kinase (CDK) is expressed and the cell cycle is inhibited thereby, resulting in proliferation inhibition. Therefore, certain HDAC inhibitor species are considered to serve as drugs causing cell differentiation or morphological normalization and the development thereof as anticancer agents has been attempted (cf. Non-Patent Documents 1 and 2). It is known that such apoptosis-inhibiting proteins as survivin, Bcl-xL and Bcl-2 are expressed at high levels in many cancer cells, and the cell death due to starvation stress caused by excessive proliferation or cell-damaging stress caused by radiation or an anticancer agent is thereby avoided. Certain HDAC inhibitors are known to reduce the expression of such apoptosis-inhibiting proteins and promote the death of cancer cells.

On the other hand, HDAC inhibitors are expected not only as anticancer agents but also as cancer-preventing drugs. It is reported that trichostatin A, suberoylanilide hydroxamic acid (SAHA) and the like markedly suppressed the occurrence of breast cancer in chemical agent-induced cancer animal models. From a study using valproic acid, it is also known that HDAC inhibitors suppress cancer metastasis (cf. e.g. Non-Patent Document 3).

Further, aside from cancers, it has been suggested in recent years that abnormal epigenetics resulting from chemical modification of chromatin might be involved in the causes of diabetes, rheumatism and like symptomatic diseases, autoimmune diseases, infectious diseases, neurodegenerative diseases and other diseases, the incidences of which increase with aging. Histone deacetylases are enzymes playing a core role in epigenetic control and are involved in the onset of diseases via various types of gene expression. Therefore, skilled molecular designing of HDAC inhibitors may possibly lead to development of medicaments not only for cancer but also for various epigenetic abnormality-due diseases, such as diabetes and other diseases mentioned above; thus, various applications have been attempted.

There are ten or more histone deacetylase subtypes and, in recent years, it has become known that there is a close relationship between certain specific histone deacetylase subtypes and cancer. For example, it has been made clear that the tumor suppressor gene p53 playing a very important role in suppressing carcinogenesis requires acetylation of p53 itself for its performing that function (cf. Non-Patent Document 4), that HDAC1 or HDAC2 is involved in inhibiting that function (cf. Non-Patent Document 5) and that the proteins PML-RAR and PLZF-RAR involved in the onset of acute promyelocytic leukemia (APL) and Bcl-6 and like oncogenes involved in the onset of lymphoma recruit HDAC4, among others, via a nuclear corepressor and thus suppress the expression of a group of genes necessary for normal differentiation, leading to carcinogenesis (cf. e.g. Non-Patent Document 6). On the other hand, it is known that among histone deacetylase subtypes which are expressed in a tissue-specific manner, there are some playing an important role in normal tissue development or differentiation (cf. Non-Patent Document 7).

HDAC6 is an enzyme shuttling between the nucleus and cytoplasm by nuclear export and generally localized in cytoplasm. HDAC6 is expressed at high levels in the testis and so forth and is possibly involved in the differentiation of normal tissues. HDAC6 is also known to be involved in deacetylation of microtubules and control the stability of microtubules. Further, HDAC6 is a deacetylase binding to microtubules and is involved in cell motility. Therefore, HDAC6 inhibitors may serve as metastasis inhibitors.

Histone deacetylases are hydrolases having a zinc atom at the active center thereof and the known agents inhibiting them mostly contain a hydroxamic acid group or a thiol group as a ligand for zinc. Therefore, the structural variety of the inhibitors is restricted and specific inhibitors capable of distinguishing histone deacetylase subtypes from one another have been developed only to an unsatisfactory extent. As regards inhibitors resulting from introduction, into cyclic tetrapeptides, of an atomic group forming a coordination bond with the zinc ion at the active center of histone deacetylases, several findings and proposals have been reported. As regards novel compounds having histone deacetylase-inhibiting activity, there are a number of patent documents concerning cyclic tetrapeptide derivatives, for instance (cf. Patent Documents 1-7 and Non-Patent Document 8). Among them, some compounds synthesized have potent enzyme-inhibiting activity; they are, however, not satisfactory from the viewpoint of toxicity or continued administration characteristics (stability against metabolism and absorbability), and none has been put into practical use as a medicament.

Patent Document 1: Japanese Patent No. 3494624
Patent Document 2: Japanese Kokai (laid-open) Publication 200-256397
Patent Document 3: Japanese Kohyo (laid open under PCT) Publication 2002-527449
Patent Document 4: Japanese Kohyo Publication 2003-505417
Patent Document 5: Japanese Kohyo Publication 2005-517683
Patent Document 6: WO 2003-70754
Patent Document 7: WO 2004-113366
Non-Patent Document 1: Nakajima, H., Kim, Y. B., Terano, H., Yoshida, M., and Horinouchi, S. (1998) FR901228, a potent antitumor antibiotic, is a novel histone deacetylase inhibitor. Exp. Cell Res. 241, 126-133
Non-Patent Document 2: Saito, A., Yamashita, T., Mariko, Y., Nosaka, Y., Tsuchiya, K., Ando, T., Suzuki, T., Tsuruo, T., and Nakanishi, O. (1999) A synthetic inhibitor of histone deacetylase, MS-27-275, with marked in vivo antitumor activity against human tumors. Proc. Natl. Acad. Sci. USA 96, 4592-4597
Non-Patent Document 3: Gottlicher, M., Minucci, S., Zhu, P., Kramer, O. H., Schimpf, A., Giavara, S., Sleeman, J. P., Lo Coco, F., Nervi, C., Pelicci, P. G., and Heinzel, T. (2001) Valproic acid defines a novel class of HDAC inhibitors inducing differentiation of transformed cells. EMBO J. 20: 6969-6978
Non-Patent Document 4: Ito, A., Lai, C. H., Zhao, X., Saito, S., Hamilton, M. H., Appella, E., and Yao, T. P. (2001) p300/CBP-mediated p53 acetylation is commonly induced by p53-activating agents and inhibited by MDM2. EMBO J. 20, 1331-1340
Non-Patent Document 5: Juan, L. J., Shia, W. J., Chen, M. H., Yang, W. M., Seto, E., Lin, Y. S., and Wu, C. W. (2000) Histone Deacetylases Specifically Down-regulate p53-dependent Gene Activation. J. Biol. Chem. 275, 20436-20443
Non-Patent Document 6: Dhordain P., Albagli, O., Lin, R. J., Ansieau, S., Quief, S., Leutz, A., Kerckaert, J. P., Evans, R. M., and Leprince, D. (1997) Corepressor SMRT binds the BTB/POZ repressing domain of the LAZ3/BCL6 oncoprotein. Proc. Natl. Acad. Sci. USA 94, 10762-10767
Non-Patent Document 7: McKinsey, T. A., Zhang, C. L., Lu, J., and Olson, E. N. (2000) Signal-dependent nuclear export of a histone deacetylase regulates muscle differentiation. Nature 408, 106-111
Non-Patent Document 8: Furumai, R., Matsuyama, A., Kobashi, N., Lee, K.-H., Nishiyama, M., Nakajima, H., Tanaka, A., Komatsu, Y., Nishino, N., Yoshida, M., and Horinouchi, S. (2002) FK228 (depsipeptide) as a natural prodrug that inhibits class I histone deacetylases. Cancer Res. 62, 4916-4921

DISCLOSURE OF INVENTION

Problems to be Solved by the Invention

Many of the existing histone deacetylase inhibitors contain, as a functional atomic group, a hydroxamic acid group highly capable of binding to the zinc atom at the active center of histone deacetylases; however, the hydroxamic acid group can form a complex with the free iron ion and is expected to show hematotoxicity. Such inhibitors may be used as anticancer agents but the application thereof in other diseases, in particular in such chronic diseases as diabetes and neural inflammations, is hesitated. Further, alkylthiolate anion groups bind to the zinc atom relatively firmly and, therefore, mercaptans are also known to show potent inhibitory activity against histone deacetylases. However, the thiol group is reactive with cystine-containing proteins through the disulfide exchange reaction, possibly producing adverse effects.

Accordingly, an object of the present invention is to newly develop effective ligands for zinc by combining those functional groups which have never been thought of and which are stable in vivo and scarcely cause adverse reactions, efficiently introduce these into various cyclic peptides showing histone deacetylase paralog specificity and thereby provide novel compounds having histone deacetylase-inhibiting activity by far higher than the conventional inhibitors and having minimal adverse effects. An another object of the invention is to provide a pharmaceutical composition comprising such a histone deacetylase inhibitor substance as an active ingredient.

Means for Solving the Problems

The present inventors made intensive investigations to accomplish the above problems; they created various cyclic tetrapeptide derivatives having a carbonyl, sulfide, sulfoxide or ether group or bond in a side chain and found that these cyclic tetrapeptide derivatives reversibly inhibit the histone deacetylase activity and show a promotion of the expression of the cell cycle inhibitor protein p21 and an inhibitory activity against the expression of the apoptosis inhibitor proteins survivin and Bcl-xL; such findings have led to completion of the present invention. Thus, the invention provides a compound having histone deacetylase-inhibiting activity which is a cyclic tetrapeptide derivative represented by the general formula (1) given below. Pharmaceutically acceptable salts of the below cyclic tetrapeptide derivative also fall within the scope of the invention. Such compound can be produced by the process to be described later herein, and the invention also includes, within the scope thereof, the use, as a medicament, of a histone deacetylase inhibitor (hereinafter sometimes referred to also as "HDAC inhibitor") which comprises the thus-obtained cyclic tetrapeptide derivative or a pharmaceutically acceptable salt thereof as an active ingredient.

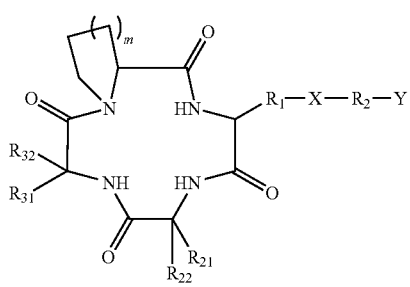

(1)

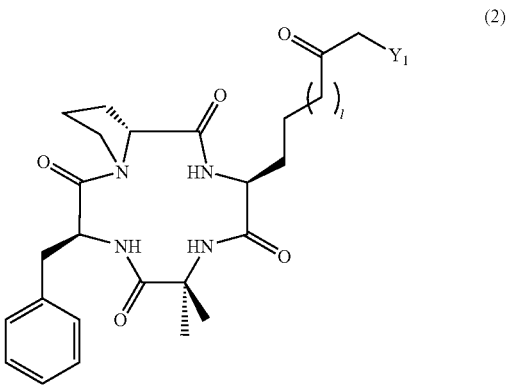

(2)

(In the above formula, l represents an integer of 1, 2, 3 or 4 and $Y_1$ represents a halogen atom, —$OCH_3$, —$OCH_2CH_3$, —$OCH_2CF_3$, —$SCH_3$, —$SCOCH_3$ or —$N(CH_3)_2$.)

Those in which $Y_1$ is Br or —$OCH_3$ or —$OCH_2CH_3$ are preferred among others since they have potent HDAC-inhibiting activity.

Further preferred in the practice of the invention are those cyclic tetrapeptide derivatives having a sulfide bond-, sulfoxide group- or ether bond-containing side chain which are represented by the general formula (3) given below.

(In the above formula, $R_1$ and $R_2$ each independently represents an alkylene group containing 1 to 6 carbon atoms, which may optionally be branched; X represents a group or bond selected from among —CO—, —O—, —S— and —SO—; Y represents a hydrogen atom, a halogen atom, a phenyl group which may optionally be substituted, a pyridyl group which may optionally be substituted, an alkyl or haloalkyl group containing 1 to 6 carbon atoms, an alkyloxy or haloalkyloxy group containing 1 to 6 carbon atoms, an alkylcarbonyl or haloalkylcarbonyl group containing 1 to 6 carbon atoms, an alkyloxycarbonyl or haloalkyloxycarbonyl group containing 1 to 6 carbon atoms, an alkylthio group containing 1 to 6 carbon atoms, an alkylthiocarbonyl group containing 1 to 6 carbon atoms or a mono- or dialkylamino group containing 1 to 6 carbon atoms; when Y is a phenyl group which may optionally be substituted or a pyridyl group which may optionally be substituted, it may form a further cyclic structure together with $R_2$; $R_{21}$, $R_{22}$, $R_{31}$ and $R_{32}$ each independently represents a monovalent atom or group selected from among a hydrogen atom, a straight alkyl group containing 1 to 6 carbon atoms, a branched alkyl group containing 3 to 6 carbon atoms, a carboxyalkyl group containing 1 to 4 carbon atoms, a straight ω-aminoalkyl group containing 1 to 5 carbon atoms, a branched aminoalkyl group containing 3 to 5 carbon atoms, a benzyl group, a substituted benzyl group and a pyridyl-substituted methyl group; and m represents an integer of 1 or 2.)

Referring to the cyclic tetrapeptide derivative represented by the above general formula (1), it is particularly preferred that $R_{21}$, $R_{22}$, $R_{31}$ and $R_{32}$ each independently represents a hydrogen atom, a straight alkyl group containing 1 to 6 carbon atoms, a branched alkyl group containing 3 to 6 carbon atoms, a straight ω-aminoalkyl group containing 1 to 5 carbon atoms, a carboxyalkyl group containing 1 to 4 carbon atoms, a benzyl group or a substituted benzyl group and m represents an integer of 1 or 2.

Also preferred in the practice of the invention are those cyclic tetrapeptide derivatives having a carbonyl group-containing side chain which are represented by the general formula (2) given below.

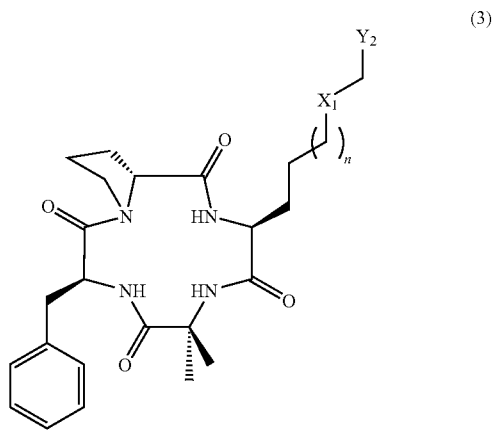

(3)

(In the above formula, n represents an integer or 1, 2, 3 or 4, $X_1$ represents —S—, —SO— or —O— and $Y_2$ represents a hydrogen atom, —$COCF_3$, —$COCH_3$, —$COCH_2OCH_3$, a phenyl group or a 2-, 3- or 4-pyridyl group.)

Effects of the Invention

The invention provides a novel cyclic tetrapeptide compound showing the highest level of activity against histone deacetylases so far by combining atomic groups in such a manner that has never been thought of. The compound of the invention is different in functional structure from those so far known in the art; thus, it becomes possible to increase the structural variety of histone deacetylase inhibitors and create high-activity, high-specificity histone deacetylase inhibitors by far surpassing those known in the art.

BEST MODES FOR CARRYING OUT THE INVENTION

Figure 1:
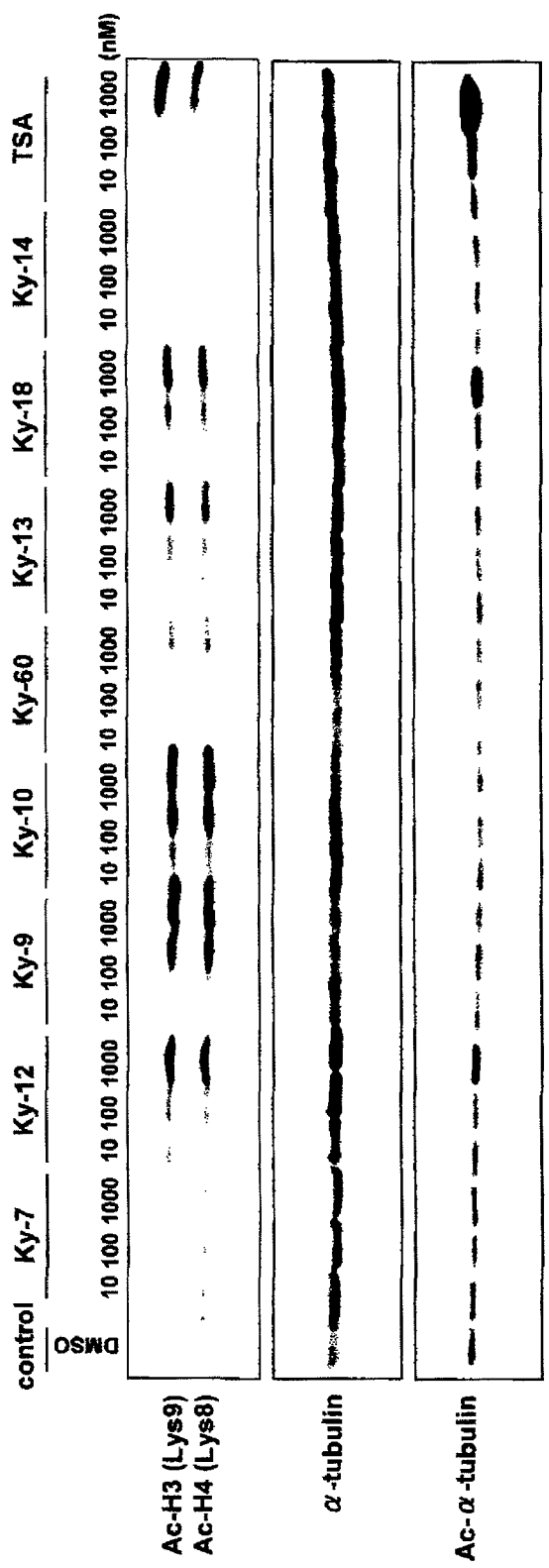
FIG. 1 shows the HDAC-inhibiting activity of each of several compounds according to the invention.
Figure 2:
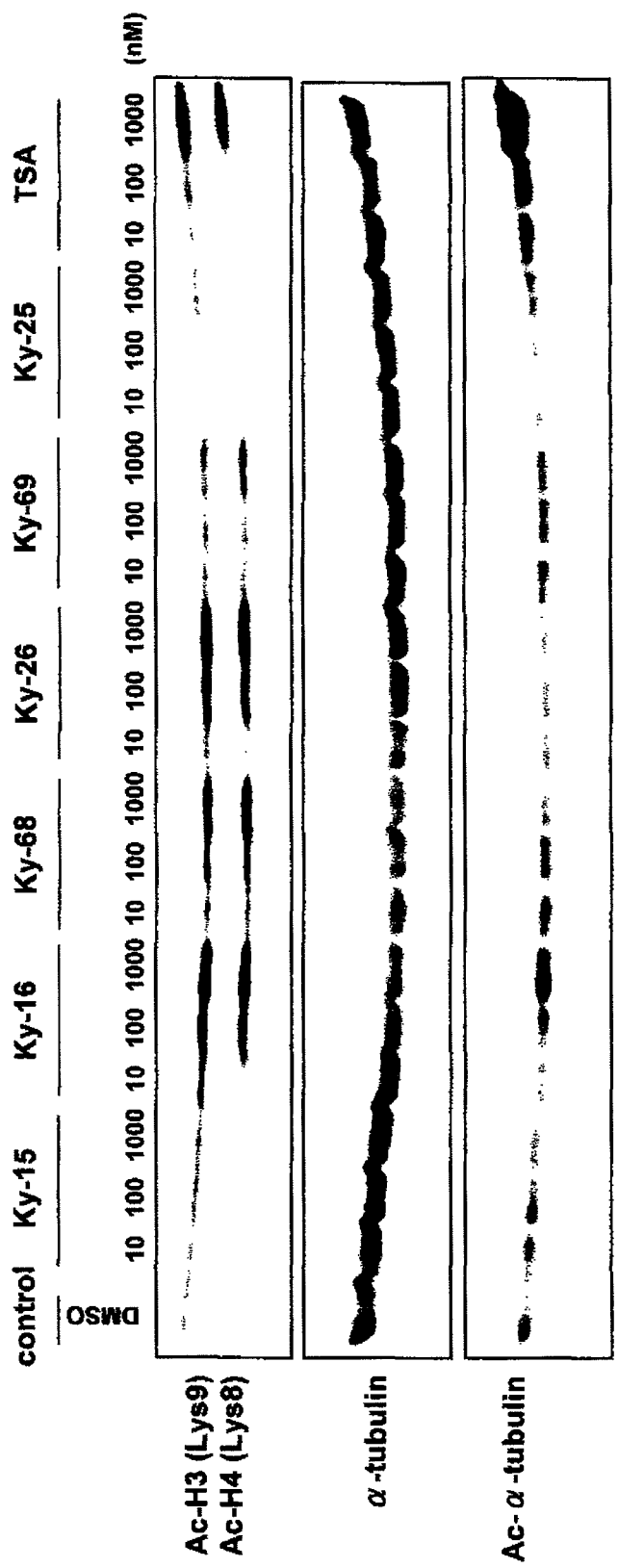
FIG. 2 shows the HDAC-inhibiting activity of each of other several compounds according to the invention.
Figure 3:
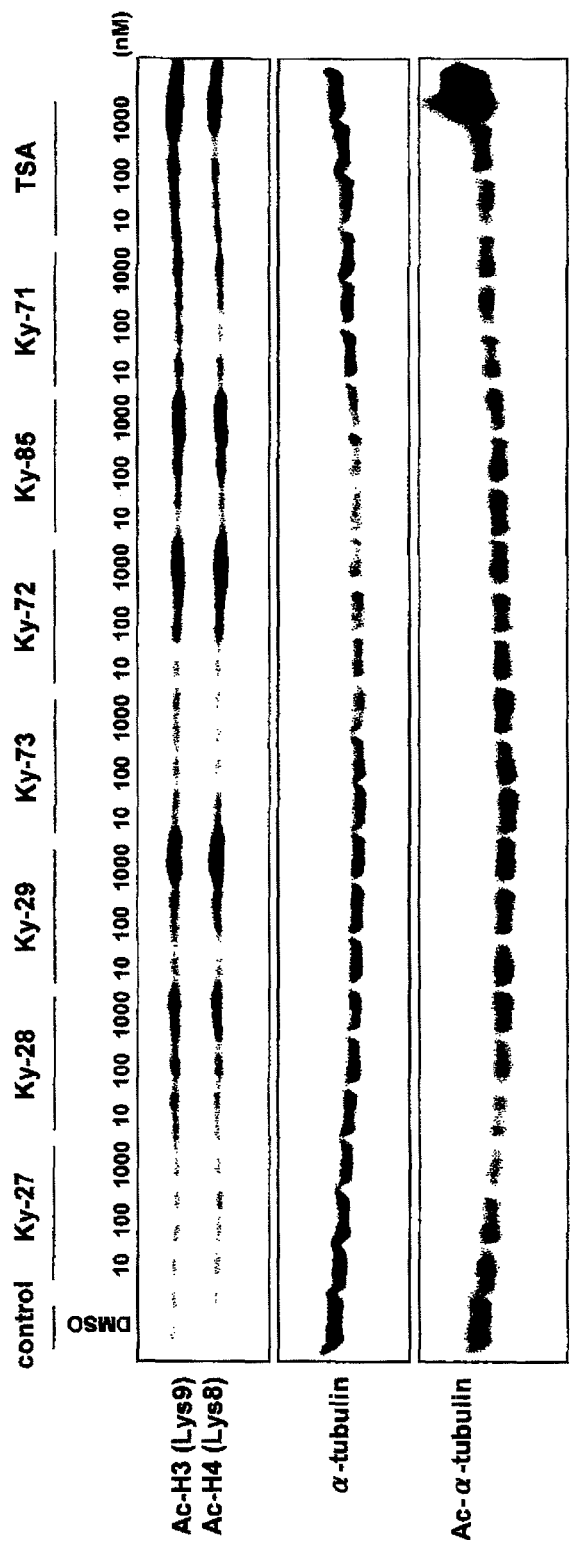
FIG. 3 shows the HDAC-inhibiting activity of each of further several compounds according to the invention.
Figure 4:
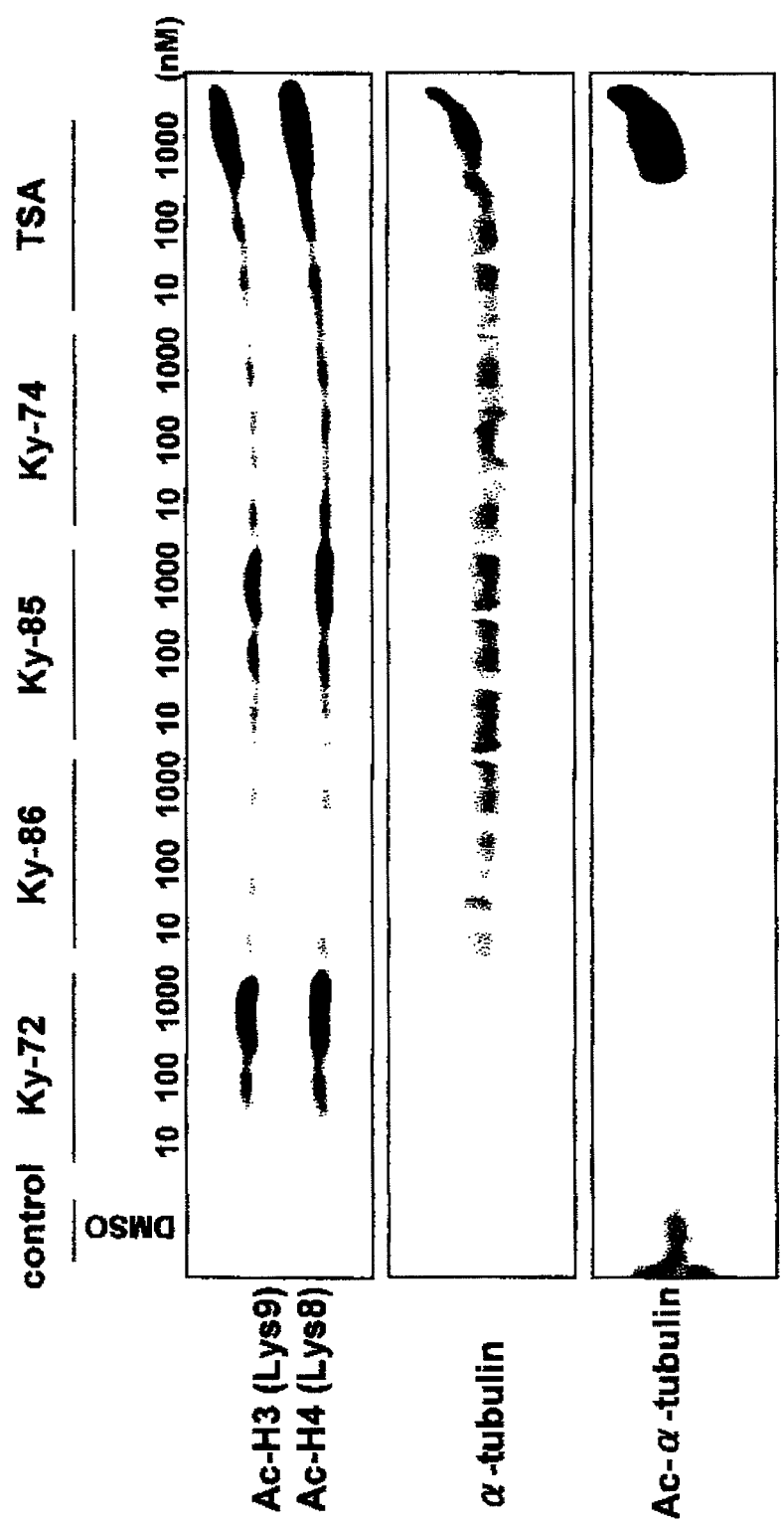
FIG. 4 shows the HDAC-inhibiting activity of each of still further several compounds according to the invention.

In the practice of the invention, those cyclic tetrapeptide derivatives which have a carbonyl group-containing side chain as expressed by the above general formula (2) are preferred among the compounds represented by the above general formula (1). The ketone carbonyl group is a functional group capable of directly acting on the active center of histone deacetylases. Also known are carbonyl group-containing cyclic tetrapeptides, such as apicidin, FR225497, TAN-1746s and 9,10-desepoxy-9-hydroxy-chlamydocin, which have been found as metabolites produced by microorganisms and show histone deacetylase-inhibiting activity. However, unlike trichostatin A (TSA) and trapoxin (TPX), which have opened the way for deacetylase inhibitors, there is no evidence for the carbonyl group thereof firmly binding to the zinc atom occurring at the active center of the enzymes and the carbonyl group is incapable of serving as a strong electrophilic group against the reactive nucleophilic group occurring in the vicinity of the active center; the relationship between inhibitory activity and structure has not been clarified.

A large number of apicidin derivatives have so far been synthesized and evaluated as histone deacetylase inhibitors. Also proposed are various compounds containing the special amino acid terminus of chlamydocin-related cyclic tetrapeptides (cf. the above-cited Patent Documents 3 and 5). Apart from those technologies, the present inventors found out a novel method of synthesizing various useful cyclic tetrapeptide-based carbonyl compounds with ease. This method going through creation of unprecedented artificial amino acids, comprises acquisition of high purity optical isomers, simple and easy peptide synthesis using only a few protective groups, an easy cyclization reaction and high efficiency functional group conversion and thus has achieved technological improvements. The compound of the invention as synthesized by such method has inhibitory activity against histone deacetylases (HDAC1, HDAC4, HDAC6) and further has p21 promoter inducing activity and, in addition, has histone H4 acetylation enhancing activity.

The characteristic feature of the side chain carbonyl compound introduced into the cyclic tetrapeptide is considered as follows. Apicidin, for example, which has a ketone carbonyl group at the cyclic tetrapeptide amino acid side chain terminus, inhibits the histone deacetylase activity like trapoxin. The cyclic tetrapeptide FR235222 has a hydroxyl group on the carbon atom neighboring the carbonyl group of apicidin; thus, it has a hydroxymethyl ketone structure. These can be considered as metabolites resulting from reduction of the epoxyketone atomic group of trapoxin and the like. However, for enhancing the inhibitory activity of the simple ketone group and simultaneously securing the stability thereof, it is necessary to introduce an electrophilic group, such as an alkoxymethyl, alkylthiomethyl or dialkylaminomethyl group, onto the carbon atom neighboring the carbonyl group. From such viewpoints, the carbonyl compound represented by the above general formula (2) is a preferred one.

In the practice of the present invention, those cyclic tetrapeptide derivatives which have a sulfide, sulfoxide or ether group or bond in the side chain as represented by the above general formula (3) are also preferred. Like the anticancer agent FK228 (Astellas Pharma), those which have a disulfide bond in the molecule to be reduced in cells to form a thiol group serving as a strong ligand for zinc are also known. On the other hand, it is also known that a sulfide bond is incapable of coordination while a thiol group is a good ligand for zinc. The thiol group, by its nature, is readily bound oxidatively to a free thiol group of a protein; hence, disadvantageously, the pharmacodynamic effect is hardly stabilized.

In the investigations made by the present inventors, they found, as a result of combining a carbonyl group with an ordinary sulfide bond across one methylene group for increasing the polarization of the carbonyl group, that the combination —$CH_2$—S—$CH_2$—CO—, for example, is effective for that purpose. Thioether compounds resulting from combination with an aromatic ring also showed potent histone deacetylase-inhibiting activity. And, the inventors found out those sulfide, sulfoxide or ether bond- or group-containing cyclic tetrapeptide derivatives represented by the above general formula (3) as compounds having particularly preferable histone deacetylase-inhibiting activity.

While the thiol group is highly reactive in the form of a thiolate, the sulfide bond or sulfoxide group is not involved in metal ion binding or disulfide exchange reactions. Attempts were made to realize a synergism-due potent inhibitory activity by combining an aromatic atomic group occupying a hydrophobic space near the zinc atom in histone deacetylases in the vicinity of the sulfide bond or sulfoxide group having only a weak binding activity or introducing a ketone carbonyl group thereinto. As a result, in particular cyclic tetrapeptide derivatives having a sulfide, sulfoxide or ether bond or group in a side chain thereof as represented by the above general formula (3) were newly developed as ligands for the zinc atom occurring in the active center of histone deacetylases and, at the same time, the production of such was also made by efficient introduction thereof into various cyclic peptides which brought about histone deacetylase paralog specificity.

In the following, the method of producing the compound having histone deacetylase-inhibiting activity according to the invention is described. First, the cyclic tetrapeptide derivative represented by the general formula (1) according to the invention is prepared by once connecting the four constituent amino acids to give the corresponding linear tetrapeptide derivative and then cyclizing this linear tetrapeptide derivative. Thus, the following four amino acids are used.

An α-amino acid represented by the general formula (4) (in the formula, $R_{21}$ and $R_{22}$ represent the same groups as $R_{21}$ and $R_{22}$ in the general formula (1)):

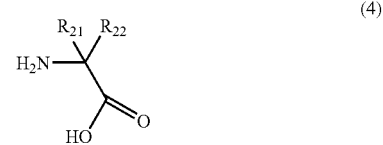

(4)

An α-amino acid represented by the general formula (5) (in the formula, $R_{31}$ and $R_{32}$ represent the same groups as $R_{31}$ and $R_{32}$ in the general formula (1)):

(5)

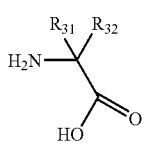

An α-amino acid represented by the general formula (6) (in the formula, m represents the same numerical value as m in the general formula (1)):

(6)

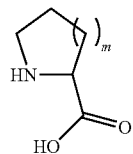

A terminal double bond-containing α-amino acid represented by the general formula (7) (in the formula, $R_1$ represents the same group as $R_1$ in the general formula (1)):

(7)

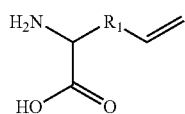

These four α-amino acids represented by the general formulas (4) to (7) are connected via peptide bonding to prepare the corresponding linear tetrapeptide derivative and then this linear tetrapeptide derivative is cyclized. After formation of the cyclic tetrapeptide skeleton, the side chain double bond occurring in the above general formula (7) can be utilized to derive a ketone or thioether therefrom.

The α-amino acids constituting the cyclic peptide of the invention which is represented by the general formula (1) each may have an L-form or D-form configuration. From the structural stability viewpoint, however, it is preferred that at least one amino acid residue is different in configuration from the remaining amino acid residues. More specifically, it is recommended that at least one or two of these four α-amino acids have the D-form and the remaining ones have the L-form. In cases where the α-amino acid having a cyclic structure including the a carbon atom is not branched, it is optically inactive and, in that case, it is desired that either one of the amino acids of the general formulas (5) and (6) is in the D-form.

More preferably, a selection is made so that, among the four amino acids mentioned above, the one represented by the general formula (6) is in the D form and the remaining three are in the L form or that those represented by the general formulas (4) and (6) are in the D form and the remaining two are in the L form.

For producing the cyclic tetrapeptide derivative of the present invention, an intermediate linear tetrapeptide resulting from successive binding, via peptide linkage, of four α-amino acids respectively represented by the general formulas (4)-(7) is once prepared and then this is converted to the corresponding cyclic tetrapeptide, which is finally derivatized into a cyclic tetrapeptide derivative of the invention which is represented by the general formula (1) and has a carbonyl group, sulfide bond, sulfoxide group or ether bond in a side chain thereof. Methods of producing cyclic tetrapeptides themselves are known in the art and are described, for example, in Patent Documents 1-7, and they can be produced by such known methods.

For example, a cyclic tetrapeptide derivative represented by the general formula (8) given below serves as an intermediate for the synthesis of a cyclic tetrapeptide derivative as defined in Claim 1 or Claim 2.

(8)

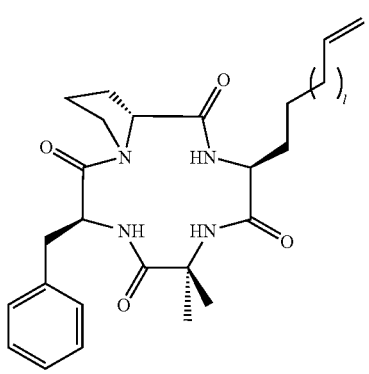

(In the above formula, 1 represents an integer of 1, 2, 3 or 4.)

The double bond at the side chain terminus in the cyclic tetrapeptide derivative of the above formula (8) can be modified by such reactions as epoxidation and acyl or like group introduction to give a side chain carbonyl group-containing cyclic tetrapeptide derivative as defined in Claim 2. A specific example of the method of producing the cyclic tetrapeptide derivative of the formula (8) is given in Example 1.

A cyclic tetrapeptide derivative having a sulfide bond-, sulfoxide group- or ether bond-containing side chain as defined in Claim 3 can be produced by introducing an amino acid having a halogen atom at the side chain terminus thereof into an appropriate cyclic tetrapeptide derivative, followed by successive functional group conversions to form a sulfide bond, sulfoxide group or ether bond.

The cyclic tetrapeptide derivative having a sulfide bond-, sulfoxide group- or ether bond-containing side chain as defined in Claim 3 can also be produced by introducing an amino acid having a halogen atom at the side chain terminus thereof into an appropriate cyclic tetrapeptide derivative, followed by glycidyl (thio)ether group introduction by successive functional group conversions, further followed by successive functional group conversions to form a sulfide bond, sulfoxide group or ether bond.

The pharmaceutically acceptable salt of the cyclic tetrapeptide derivative of the invention, when it is, for example, a derivative containing a nitrogen atom showing basicity, includes salts with such inorganic acids as hydrochloric acid, hydrobromic acid, phosphoric acid, sulfuric acid and nitric acid as well as salts with such organic acids as acetic acid, lactic acid, tartaric acid, fumaric acid, maleic acid, trifluoroacetic acid, methanesulfonic acid, benzenesulfonic acid and toluenesulfonic acid.

The cyclic tetrapeptide derivative of the invention or a pharmaceutically acceptable salt thereof can be utilized as an active ingredient of a histone deacetylase inhibitor or a like medicament. The compound of the invention has an inhibitory activity on various types of histone deacetylase, as shown in Examples 24-26.

The pharmaceutical composition comprising, as an active ingredient, the cyclic tetrapeptide derivative of the invention or a pharmaceutically acceptable salt thereof is advantageous in that it not only induces the expression of the cell cycle inhibitor protein p21 causing cancer cell proliferation inhibition through changes in gene expression pattern due to the very histone deacetylase inhibition but also produces a significant therapeutic effect in synergy with the cancer cell apoptosis inducing and stress susceptibility enhancing effects due to reduced expression of apoptosis inhibiting proteins such as survivin and Bcl-xL. In addition, when compared with trapoxin analogs, which are irreversible inhibitors, unfavorable residual influences on the living body, such as adverse effects on normal tissue cells, of the cyclic tetrapeptide derivative mentioned above remain to a lesser extent; hence, from the therapeutic effect viewpoint as well, the above pharmaceutical composition is expected to be applicable as a drug markedly reduced in relative adverse effect level.

The dose of the cyclic tetrapeptide derivative to serve as an active ingredient in the pharmaceutical composition of the invention is to be properly selected according to the object of treatment, the severity of symptoms and the sex, age and body weight of the administration subject, among others. In the case of the administration subject being an adult male, the daily dose is selected generally within the range of 0.01-50 mg/kg, preferably within the range of 0.5-10 mg/kg, and it may be administered as a single dose or as several divided doses. The pharmaceutical composition of the invention can have a dosage form suited for the intended route of administration as prepared by adding an additive or additives commonly used in peptide-like compound preparations of this kind to the cyclic tetrapeptide derivative or a pharmaceutically acceptable salt thereof, which serves as an active ingredient. Since the derivative is outstanding in cell-penetrating ability, various routes of administration can be utilized; those dosage forms and routes of administration which are frequently used in the administration of peptide hormones and the like are preferably employed.

EXAMPLES

The following examples illustrate the present invention in detail. In the following description, L-Ae9 is an abbreviation for S-2-amino-8-nonenoyl. Examples are given in which a number of cyclic tetrapeptide derivatives of the invention which have a carbonyl group in a side chain are derived by introducing this amino acid group into the cyclic tetrapeptide skeleton of chlamydocin and then variously modifying the double bond at the side chain terminus via an epoxide, bromohydrin, etc.

The functional groups newly introduced are specified by putting the respective abbreviations thereof in parentheses as follows: bromomethyl ketone: Ae9(Bmk); methoxymethyl ketone: Ae9(Mmk); ethoxymethyl ketone: Ae9(Emk); trifluoroethoxymethyl ketone: Ae9(Tfemk); methylthiomethyl ketone: Ae9(Mtmk); acetylthiomethyl ketone: Ae9(Actmk); dimethylaminomethyl ketone: Ae9(Dmamk).

L-Ab5, L-Ab6, L-Ab7 and L-Ab8 are abbreviations for S-2-amino-5-bromopentanoyl, S-2-amino-6-bromohexanoyl, S-2-amino-7-bromoheptanoyl and S-2-amino-8-bromooctanoyl, respectively.

L-Am5, L-Am6, L-Am7 and L-Am8 are abbreviations for S-2-amino-5-mercaptopentanoyl, S-2-amino-6-mercaptohexanoyl, S-2-amino-7-mercaptoheptanoyl and S-2-amino-8-mercaptooctanoyl, respectively.

Those various atomic groups which are to be bound to the sulfur atom in those groups are alkyl groups or modified aryl groups, such as methyl, benzyl and pyridylmethyl, as indicated in parentheses. In the case of further oxidation of the sulfide bond resulting from alkylation of such sulfur atom, this is indicated by the term "sulfoxide" in parentheses. L-Ah7 is an abbreviation for S-2-amino-7-hydroxyheptanoyl and the alkyl group employed to modify the terminal oxygen thereof is indicated in parentheses. Aib is an abbreviation for 2-aminoisobutyric acid.

Reference Example 1

Synthesis of t-butyloxycarbonyl-S-2-amino-8-nonenoic acid (Boc-L-Ae9-OH)

Diethyl Boc-aminomalonate (15.2 g, 55.0 mmol) was dissolved in absolute ethanol containing an equimolar amount of sodium ethoxide, 7-bromo-1-heptene (8.64 ml, 10.0 g, 55.0 mmol) was added, and the mixture was refluxed for 5 hours. A 1 M sodium hydroxide solution (60 ml) was added and, after effecting half-saponification and after sufficient acidification, the product half ester-half carboxylic acid was extracted with toluene. The toluene solution was dried over anhydrous magnesium sulfate and then refluxed for 6 hours for effecting decarboxylation, and the product Boc-DL-Ae9-OEt was purified by silica gel chromatography using 1% methanol/chloroform (12.1 g, 40.4 mmol, 73%). Further, this was suspended in DMF (dimethylformamide) (40 ml) and water (40 ml), and subtilisin (45 mg) was added for effecting selective hydrolysis. While the enzymatic reaction was in progress, the pH was maintained at around 8 using 1 M aqueous ammonia. The optical resolution product Boc-L-Ae9-OH was extracted with ethyl acetate under acidic conditions of pH 3, the extract was dried, and the solvent was distilled off to give colorless transparent liquid. The yield was 4.88 g (45%).

HPLC: rt: 7.64 min. (column: Chromolith Performance RP-18e, 4.6 mm×100 mm, 10-100% linear gradient $CH_3CN$/0.1% TFA over 15 min, flow rate 2.0 ml/min. The HPLC conditions were the same in the subsequent examples as well.) $[\alpha]^{25}_D = -3.1$ (c=1, MeOH). HR-FAB MS $[M+H]^+$ 272.1893 for $C_{14}H_{26}O_4N$ (calcd. 272.1862). $^1$H NMR (500 MHz, $CDCl_3$) $\delta_H$=1.29-1.39 (6H, m, γ, δ and ε), 1.45 (9H, s, t-Bu), 1.67 and 1.86 (1H, each, each, m, β), 2.06 (2H, m, C$H_2$CH=$CH_2$), 4.29 (1H, m, α), 4.92-5.01 (3H, m, NH and C$H_2$CH=$CH_2$), 5.79 (1H, ddt, J=17.2, 10.2, 6.5, $CH_2$CH=$CH_2$), $^{13}$C NMR ($CDCl_3$) $\delta_c$=25.15 (γ-C), 28.32 (($CH_3)_3C$—), 28.62 (δ-C and ε-C), 32.28 (β-C), 33.60 (ω-C), 53.39 (α-C), 80.22 (($CH_3)_3C$—), 114.43 ($CH_2$—CH=$CH_2$), 138.83 ($CH_2$—CH=$CH_2$), 163.06 (C=O, -Boc), 176.78 (C=O, —COOH).

Reference Example 2

Synthesis of Boc-L-Ae9-Aib-L-Phe-D-Pro-OtBu

Boc-L-Ae9-OH (5.43 g, 20 mmol) obtained in Reference Example 1 was condensed with H-Aib-L-Phe-D-Pro-OtBu (8.07 g, 20 mmol) in the conventional manner of peptide synthesis, and the product was extracted with ethyl acetate and purified by silica gel flash chromatography using 1% methanol/chloroform (12.3 g, 18.8 mmol, 94%). HPLC: rt: 11.16 min. HR-FABMS $[M+H]^+$ 657.4270 for $C_{36}H_{57}O_7N_4$ (calcd. 657.4227).

Example 1

Synthesis of cyclo(-L-Ae9-Aib-L-Phe-D-Pro-)

Compound (Ky-17) of the above formula (8) in which l=3. In Table 1 and FIG. 1, each compound is specified by an abbreviation therefor. The compound in this example is Ky-17 (hereinafter the same shall apply.)

Boc-L-Ae9-Aib-L-Phe-D-Pro-OtBu (12.3 g, 18.8 mmol) obtained in Reference Example 2 was treated with TFA (trifluoroacetic acid) (50 ml) at 0° C. for 3 hours to thereby eliminate the protective groups at both ends. After distilling off the TFA, the residue was solidified with ether to give the TFA salt as a powder (11.6 g, 100%). HPLC: rt: 5.96 min. HR-FABMS [M+H]$^+$, 501.3050 (calcd. 501.3077, $C_{27}H_{41}O_5N_4$).

This TFA salt (4.92 g, 8.0 mmol) was dissolved in DMF (20 ml) and subjected, in 5 divided portions at 30-minute intervals, to the cyclization reaction using the condensation reagent HATU (O-(7-azabenzotriazol-1-yl)-N,N,N',N'-tetramethyluronium hexafluorophosphate) (3.64 g, 9.6 mmol) and diisopropylethylamine (4.45 ml, 25.6 mmol) at room temperature in 800 ml of DMF in a dilute condition of 5 mM. The solvent was distilled off, and the residue was extracted with ethyl acetate and purified by silica gel chromatography (1% methanol/chloroform). A colorless solid 3.36 g (87%) was obtained.

HPLC: rt: 9.34 min., HR-FAB MS [M+H]$^+$ 483.2971 for $C_{27}H_{39}O_4N_4$ (calcd. 483.2971). $^1$H NMR (500 MHz, CDCl$_3$): $\delta_H$=1.28 (m, 2H), 1.32 (m, 2H), 1.34 (s, 3H), 1.38 (m, 2H), 1.63 (m, 1H), 1.73 (m, 1H), 1.76 (m, 1H), 1.77 (s, 3H), 1.80 (m, 1H), 2.03 (m, 2H), 2.18 (m, 1H), 2.32 (m, 1H), 2.95 (dd, J=13.3, 5.7 Hz, 1H), 3.23 (m, 1H), 3.26 (dd, J=13.5, 10.0 Hz, 1H), 3.86 (m, 1H), 4.18 (m, 1H), 4.66 (m, 1H), 4.97 (m, 2H), 5.16 (ddd, J=10.1, 10.1, 5.9 Hz, 1H), 5.79 (ddt, J=17.2, 10.2, 6.5, 1H), 5.91 (s, 1H), 7.08 (d, J=10.5 Hz, 1H), 7.21 (m, 3H), 7.27 (m, 2H), 7.52 (d, J=10.5 Hz, 1H).

Reference Example 3

Synthesis of cyclo(-L-Ae9(O)-Aib-L-Phe-D-Pro-) (Ky-7)

Cyclo(-L-Ae9-Aib-L-Phe-D-Pro-) (4.73 g, 9.80 mmol) obtained in Example 1 was dissolved in anhydrous dichloromethane (200 ml), a solution of metachloroperbenzoic acid (3.38 g, 19.6 mmol) in anhydrous dichloromethane (100 ml) was added under cooling with ice, and the reaction was allowed to proceed at room temperature for 18 hours. The reaction mixture was washed with 4% NaHCO$_3$ and brine, the solvent was distilled off, and the residue was purified by silica gel chromatography using 1% methanol/chloroform to give a colorless solid (4.33 g, 89%).

HPLC: rt: 7.13 min. HR-FAB MS [M+H]$^+$ 499.2891 for $C_{27}H_{39}O_5N_4$ (calcd. 499.2920), $^1$H NMR (500 MHz, CDCl$_3$): $\delta_H$=1.28 (m, 2H), 1.32 (m, 2H), 1.34 (s, 3H), 1.38 (m, 1H), 1.46 (m, 1H), 1.52 (m, 2H) 1.64 (m, 1H), 1.74 (m, 1H), 1.76 (m, 1H), 1.77 (s, 3H), 1.80 (m, 1H), 2.18 (m, 1H), 2.32 (m, 1H), 2.46 (m, 1H), 2.74 (m, 1H), 2.89 (m, 1H), 2.95 (dd, J=13.5, 6.0 Hz, 1H), 3.23 (m, 1H), 3.26 (dd, J=13.5, 10.0 Hz, 1H), 3.86 (m, 1H), 4.19 (m, 1H), 4.66 (m, 1H), 5.16 (ddd, J=10.2, 10.2, 5.8 Hz, 1H), 5.94 (s, 1H), 7.10 (d, J=10.0 Hz, 1H), 7.21 (m, 3H), 7.27 (m, 2H), 7.51 (d, J=10.5 Hz, 1H).

Reference Example 4

Synthesis of cyclo(-L-Ae9(8-OH,9-Br)-Aib-L-Phe-D-Pro-)

Cyclo(-L-Ae9(O)-Aib-L-Phe-D-Pro-) (2.49 g, 5.00 mmol) obtained in Reference Example 3 was dissolved in anhydrous THF (50 ml), glacial acetic acid (0.83 ml) and anhydrous LiBr (695 mg, 8.00 mmol) were added, and the reaction was allowed to proceed at room temperature for 5 hours. Water (1 ml) was added, the solvents were distilled off, and the residue was extracted with ethyl acetate and purified by silica gel chromatography using 2% methanol/chloroform to give a colorless solid (2.69 g, 93%).

HPLC: rt: 6.68 min. HR-FAB MS [M+H]$^+$ 579.2156 for $C_{27}H_{40}O_5N_4{}^{79}Br$ (calcd. 579.2182) and 581.2098 for $C_{27}H_{40}O_5N_4{}^{81}Br$ (calcd. 581.2162), $^1$H NMR (500 MHz, CDCl$_3$): $\delta_H$=1.30 (m, 2H), 1.31 (m, 2H), 1.34 (s, 3H), 1.35 (m, 1H), 1.46 (m, 1H), 1.54 (m, 2H), 1.63 (m, 1H), 1.74 (m, 1H), 1.77 (s, 3H), 1.79 (m, 1H), 1.80 (m, 1H), 2.09 (s, 1H), 2.17 (m, 1H), 2.32 (m, 1H), 2.95 (dd, J=13.5, 6.0 Hz, 1H), 3.21 (m, 1H), 3.26 (dd, J=13.5, 10.0 Hz, 1H), 3.38 (m, 1H), 3.53 (m, 1H), 3.77 (m, 1H), 3.85 (m, 1H), 4.20 (m, 1H), 4.67 (m, 1H), 5.16 (ddd, J=10.2, 10.2, 5.5 Hz, 1H), 6.07 (d, J=8.5 Hz, 1H), 7.14 (d, J=10.5 Hz, 1H), 7.22 (m, 3H), 7.27 (m, 2H), 7.52 (d, J=10.5 Hz, 1H).

Reference Example 5

Synthesis of cyclo(-L-Ae9 (8-OH,9-OCH$_3$)-Aib-L-Phe-D-Pro-)

Cyclo(-L-Ae9(O)-Aib-L-Phe-D-Pro-) (499 mg, 1.00 mmol) obtained in Reference Example 3 was dissolved in a 0.5 M sodium methoxide/methanol solution (2 ml), and the reaction was allowed to proceed at 28° C. for 16 hours. Acetic acid (1 ml) was added, the solvents were distilled off, and the product was extracted with ethyl acetate and purified by silica gel chromatography using a 2% methanol/chloroform solution to give a colorless solid (361 mg, 68%).

HPLC: rt: 6.27 min. HR-FAB MS [M+H]$^+$ 531.3204 for $C_{28}H_{43}O_6N_4$ (calcd. 531.3183), $^1$H NMR (500 MHz, CDCl$_3$): $\delta_H$=1.31 (m, 2H), 1.32 (m, 2H) 1.34 (s, 3H), 1.36 (m, 2H), 1.42 (m, 2H), 1.62 (m, 1H), 1.74 (m, 1H), 1.77 (s, 3H), 1.79 (m, 1H), 1.80 (m, 1H), 1.84 (br, 1H), 2.17 (m, 1H), 2.32 (m, 1H), 2.95 (dd, J=13.5, 6.0 Hz, 1H), 3.21 (m, 1H), 3.26 (dd, J=13.5, 10.0 Hz, 1H), 3.24 (m, 1H), 3.39 (m, 1H), 3.76 (m, 1H), 3.85 (m, 1H), 3.88 (s, 1H), 4.18 (m, 1H), 4.66 (m, 1H), 5.16 (ddd, J=10.2, 10.2, 5.5 Hz, 1H), 5.94 (d, J=5 Hz, 1H), 7.09 (d, J=10.5 Hz, 1H), 7.22 (m, 3H), 7.27 (m, 2H), 7.51 (d, J=10.0 Hz, 1H).

Reference Example 6

Synthesis of cyclo(-L-Ae9 (8-OH,9-OCH$_2$CH$_3$)-Aib-L-Phe-D-Pro-)

Cyclo(-L-Ae9(O)-Aib-L-Phe-D-Pro-) (499 mg, 1.00 mmol) obtained in Reference Example 3 was dissolved in a 0.5 M sodium ethoxide/ethanol solution (2 ml), and the reaction was allowed to proceed at 28° C. for 16 hours. Acetic acid (1 ml) was added, the solvents were distilled off, and the product was extracted with ethyl acetate and purified by silica gel chromatography using a 2% methanol/chloroform solution to give a colorless solid (381 mg, 70%). HPLC: rt: 6.85 min.

Reference Example 7

Synthesis of cyclo(-L-Ae9 (8-OH,9-OCH$_2$CF$_3$)-Aib-L-Phe-D-Pro-)

In an argon atmosphere, metallic sodium (230 mg, 10.0 mmol) was dissolved in trifluoroethanol (10 ml). In the resulting sodium trifluoroethoxide solution (5 ml) was dissolved cyclo(-L-Ae9(O)-Aib-L-Phe-D-Pro-) (499 mg, 1.00 mmol)

obtained in Reference Example 3, and the reaction was allowed to proceed at 38° C. for 48 hours. Acetic acid (1 ml) was added, the solvents were distilled off, and the product was extracted with ethyl acetate and purified by silica gel chromatography using a 1% methanol/chloroform solution to give a colorless solid (449 mg, 75%).

HPLC: rt: 7.33 min. HR-FAB MS [M+H]$^+$ 599.3058 for $C_{29}H_{42}O_6N_4F_3$ (calcd. 599.3056), $^1$H NMR (500 MHz, $CDCl_3$) $\delta_H$=1.34 (m, 8H), 1.44 (m, 2H), 1.59 (m, 2H), 1.63 (m, 1H), 1.74 (m, 1H), 1.77 (s, 3H), 1.79 (m, 1H), 1.80 (m, 1H), 2.17 (m, 1H), 2.32 (m, 1H), 2.95 (dd, J=13.5, 6.0 Hz, 1H), 3.21 (m, 1H), 3.46 (m, 1H), 3.65 (m, 1H), 3.80 (m, 1H), 3.85 (m, 1H), 3.26 (dd, J=13.5, 10.0 Hz, 1H), 3.89 (m, 2H), 4.18 (m, 1H), 4.66 (m, 1H), 5.16 (ddd, J=10.2, 10.2, 5.5 Hz, 1H), 5.90 (d, J=4.5 Hz, 1H), 7.09 (d, J=10.0 Hz, 1H), 7.21 (m, 3H), 7.28 (m, 2H), 7.50 (d, J=10.5 Hz, 1H).

Example 2

Synthesis of cyclo(-L-Ae9(Bmk)-Aib-L-Phe-D-Pro-)

Compound (Ky-12) of the above formula (2) in which l=3 and $Y_1$=Br.

Cyclo(-L-Ae9(8-OH,9-Br)-Aib-L-Phe-D-Pro-) (209 mg, 0.360 mmol) obtained in Reference Example 4 was dissolved in anhydrous dichloromethane (4 ml), the Dess-Martin reagent (458 mg, 1.08 mmol) was added, and the reaction was allowed to proceed at 25° C. for 3 hours. The reaction mixture was diluted with 4 ml of diethyl ether, and a saturated $NaHCO_3$ solution containing sodium thiosulfate pentahydrate (804 mg) was added. The resulting suspension became transparent in 10 minutes and separated into two layers; the organic layer was separated, washed with water and then dried over anhydrous magnesium sulfate. The solvent was distilled off to give an oil, which was purified by silica gel chromatography. A colorless solid (185 mg, 89%) was obtained.

HPLC: rt: 7.33 min. HR-FAB MS [M+H]$^+$ 577.2051 for $C_{27}H_{38}O_5N_4{}^{79}Br$ (calcd. 577.2026) and 579.1997 for $C_{27}H_{38}O_5N_4{}^{81}Br$ (calcd. 579.2005), $^1$H NMR (500 MHz, $CDCl_3$): $\delta_H$=1.31 (m, 2H), 1.32 (m, 3H), 1.34 (s, 3H), 1.62 (m, 2H), 1.75 (m, 1H), 1.77 (s, 3H), 1.79 (m, 1H), 1.80 (m, 1H), 2.17 (m, 1H), 2.32 (m, 1H), 2.65 (t, J=7.5 Hz, 2H), 2.95 (dd, J=13.5, 6.0 Hz, 1H), 3.21 (m, 1H), 3.26 (dd, J=13.5, 10.0 Hz, 1H), 3.86 (m, 1H), 3.87 (s, 2H), 4.18 (m, 1H), 4.66 (m, 1H), 5.16 (ddd, J=10.2, 10.2, 5.5 Hz, 1H), 5.93 (s, 1H), 7.10 (d, J=10.5 Hz, 1H), 7.22 (m, 3H), 7.27 (m, 2H), 7.50 (d, J=10.5 Hz, 1H).

Example 3

Synthesis of cyclo(-L-Ae9(Mmk)-Aib-L-Phe-D-Pro-)

Compound (Ky-9) of the above formula (2) in which l=3 and $Y_1$=$OCH_3$.

Cyclo(-L-Ae9(8-OH,9-$OCH_3$)-Aib-L-Phe-D-Pro-) (318 mg, 0.600 mmol) obtained in Reference Example 5 was treated with the Dess-Martin reagent (765 mg. 1.8 mmol) in the same manner as in Example 2 to give the corresponding methoxymethyl ketone form (270 mg, 85%).

HPLC: rt: 6.16 min. HR-FAB MS [M+H]$^+$ 529.3026 for $C_{28}H_{41}O_6N_4$ (calcd. 529.3026), $^1$H NMR (500 MHz, $CDCl_3$): $\delta_H$=1.31 (m, 2H), 1.32 (m, 3H), 1.34 (s, 3H), 1.60 (m, 1H), 1.61 (m, 1H), 1.74 (m, 1H), 1.77 (s, 3H), 1.79 (m, 2H), 2.17 (m, 1H), 2.32 (m, 1H), 2.43 (t, J=7.5 Hz, 2H), 2.95 (dd, J=13.5, 6.0 Hz, 1H), 3.21 (m, 1H), 3.26 (dd, J=13.5, 10.0 Hz, 1H), 3.42 (s, 3H), 3.86 (m, 1H), 3.99 (s, 2H), 4.18 (m, 1H), 4.66 (m, 1H), 5.16 (ddd, J=10.2, 10.2, 5.5 Hz, 1H), 5.97 (s, 1H), 7.11 (d, J=10.5 Hz, 1H), 7.21 (m, 3H), 7.27 (m, 2H), 7.51 (d, J=10.5 Hz, 1H).

Example 4

Synthesis of cyclo(-L-Ae9(Emk)-Aib-L-Phe-D-Pro-)

Compound (Ky-10) of the above formula (2) in which l=3 and $Y_1$=$OCH_2CH_3$.

Cyclo(-L-Ae9(8-OH,9-$OC_2H_5$)-Aib-L-Phe-D-Pro-) (326 mg, 0.60 mmol) obtained in Reference Example 6 was subjected to Dess-Martin oxidation in the same manner as in the synthesis in Example 2, and the product was purified by silica gel chromatography to give a colorless solid (302 mg, 93%).

HPLC: rt: 7.06 min. HR-FAB MS [M+H]$^+$ 543.3223 for $C_{29}H_{43}O_6N_4$ (calcd. 543.3183), $^1$H NMR (500 MHz, $CDCl_3$): $\delta_H$=1.25 (t, J=7.0 Hz, 3H) 1.31 (m, 2H), 1.32 (m, 3H), 1.34 (s, 3H), 1.59 (m, 1H), 1.60 (m, 1H), 1.74 (m, 1H), 1.77 (s, 3H), 1.79 (m, 2H), 2.18 (m, 1H), 2.32 (m, 1H), 2.45 (t, J=7.5 Hz, 2H), 2.95 (dd, J=13.5, 6.0 Hz, 1H), 3.21 (m, 1H), 3.26 (dd, J=13.5, 10.0 Hz, 1H), 3.55 (q, J=7.0 Hz, 2H), 3.86 (m, 1H), 4.03 (s, 2H), 4.18 (m, 1H), 4.66 (m, 1H), 5.16 (ddd, J=10.2, 10.2, 5.5 Hz, 1H), 5.92 (s, 1H), 7.09 (d, J=10.5 Hz, 1H), 7.21 (m, 3H), 7.26 (m, 2H), 7.50 (d, J=10.5 Hz, 1H).

Example 5

Synthesis of cyclo(-L-Ae9(Tfemk)-Aib-L-Phe-D-Pro-)

Compound (Ky-60) of the above formula (2) in which l=3 and $Y_1$=$OCH_2CF_3$.

Cyclo(-L-Ae9(8-OH,9-$OCH_2CF_3$)-Aib-L-Phe-D-Pro-) (359 mg, 0.60 mmol) obtained in Reference Example 7 was subjected to Dess-Martin oxidation in the same manner as in the synthesis in Example 2, and the product was purified by silica gel chromatography to give a colorless solid (333 mg, 93%).

HPLC: rt: 8.01 min. HR-FAB MS [M+H]$^+$ 597.2881 for $C_{29}H_{40}O_6N_4F_3$ (calcd. 597.2900). $^1$H NMR (500 MHz, $CDCl_3$): $\delta_H$=1.31 (m, 2H), 1.32 (m, 3H), 1.34 (s, 3H), 1.60 (m, 1H), 1.61 (m, 1H), 1.74 (m, 1H), 1.77 (s, 3H), 1.79 (m, 2H), 2.18 (m, 1H), 2.32 (m, 1H), 2.44 (t, J=7.5 Hz, 2H), 2.95 (dd, J=13.5, 6.0 Hz, 1H), 3.21 (m, 1H), 3.26 (dd, J=13.5, 10.0 Hz, 1H), 3.86 (m, 1H), 3.94 (q, $J_{H,F}$=8.5 Hz, 2H), 4.18 (m, 1H), 4.22 (s, 2H), 4.66 (m, 1H), 5.16 (ddd, J=10.2, 10.2, 5.5 Hz, 1H), 5.90 (s, 1H), 7.10 (d, J=10.0 Hz, 1H), 7.22 (m, 3H), 7.27 (m, 2H), 7.49 (d, J=10.0 Hz, 1H).

Example 6

Synthesis of cyclo(-L-Ae9(Mtmk)-Aib-L-Phe-D-Pro-)

Compound (Ky-13) of the above formula (2) in which l=3 and $Y_1$=$SCH_3$.

Cyclo(-L-Ae9(Bmk)-Aib-L-Phe-D-Pro) (62 mg, 0.108 mmol) obtained in Example 2 was dissolved in DMF (0.5 ml), sodium thiomethoxide (8.0 mg, 0.108 mmol) was added, and the reaction was allowed to proceed at room temperature for 1 hour. The product was extracted with ethyl acetate and purified by silica gel chromatography (51.0 mg, 87%).

HPLC: rt: 7.22 min. HR-FAB MS [M+H]$^+$ 545.2766 for $C_{28}H_{41}O_5N_4S$ (calcd. 545.2798), $^1$H NMR (500 MHz, $CDCl_3$): $\delta_H$=1.28 (m, 2H), 1.32 (m, 2H), 1.34 (s, 3H), 1.61

(m, 2H), 1.64 (m, 1H), 1.74 (m, 1H), 2.32 (m, 1H), 1.76 (m, 1H), 1.77 (s, 3H), 1.81 (m, 1H), 2.07 (s, 3H), 2.18 (m, 1H), 2.60 (t, J=7.5 Hz, 2H), 2.95 (dd, J=13.7, 5.7 Hz, 1H), 3.16 (s, 2H), 3.23 (m, 1H), 3.26 (dd, J=14.0, 10.0 Hz, 1H), 3.86 (m, 1H), 4.18 (m, 1H), 4.66 (m, 1H), 5.16 (ddd, J=10.0, 10.0, 6.0 Hz, 1H), 5.91 (s, 1H), 7.09 (d, J=10.5 Hz, 1H), 7.21 (m, 3H), 7.28 (m, 2H), 7.50 (d, J=10.0 Hz, 1H).

Example 7

Synthesis of cyclo(-L-Ae9(Actmk)-Aib-L-Phe-D-Pro-)

Compound (Ky-18) of the above formula (2) in which l=3 and $Y_1$=—SCOCH$_3$.

Cyclo(-L-Ae9(Bmk)-Aib-L-Phe-D-Pro-) (60.0 mg, 0.104 mmol) obtained in Example 2 was dissolved in DMF (0.5 ml), potassium thioacetate (12.0 mg, 0.104 mmol) was added, and the reaction was allowed to proceed at room temperature for 3 hours. The product was extracted with ethyl acetate and purified by silica gel chromatography (47.0 mg, 79%).

HPLC: rt: 7.40 min. HR-FAB MS [M+H]$^+$ 573.2723 for $C_{29}H_{41}O_6N_4S$ (calcd. 573.2747), $^1$H NMR (500 MHz, CDCl$_3$) $\delta_H$=1.28 (m, 2H), 1.32 (m, 2H), 1.34 (s, 3H), 1.61 (m, 2H), 1.64 (m, 1H), 1.74 (m, 1H), 1.76 (m, 1H), 1.77 (s, 3H), 1.81 (m, 1H), 2.18 (m, 1H), 2.32 (m, 1H), 2.39 (s, 3H), 2.54 (t, J=7.5 Hz, 2H), 2.95 (dd, J=13.7, 5.7 Hz, 1H), 3.73 (s, 2H), 3.23 (m, 1H), 3.26 (dd, J=14.0, 10.0 Hz, 1H), 3.86 (m, 1H), 4.18 (m, 1H), 4.66 (m, 1H), 5.16 (ddd, J=10.0, 10.0, 6.0 Hz, 1H), 5.93 (s, 1H), 7.09 (d, J=10.0 Hz, 1H), 7.21 (m, 3H), 7.28 (m, 2H), 7.50 (d, J=10.0 Hz, 1H).

Example 8

Synthesis of cyclo(-L-Ae9(Dmamk)-Aib-L-Phe-D-Pro-)

Compound (Ky-14) of the above formula (2) in which l=3 and $Y_1$=N(CH$_3$)$_2$.

Cyclo(-L-Ae9(Bmk)-Aib-L-Phe-D-Pro-) (63.0 mg, 0.109 mmol) obtained in Example 2 was dissolved in absolute methanol (0.5 ml), a 2 M dimethylamine solution in methanol (82 µl, 0.160 mmol) was added, and the reaction was allowed to proceed for 5 hours. The product was extracted with ethyl acetate and purified by silica gel chromatography (40.0 mg, 68%).

HPLC: rt: 4.54 min. HR-FAB MS [M+H]$^+$ 542.3320 for $C_{29}H_{44}O_5N_5$ (calcd. 542.3342), $^1$H NMR (500 MHz, CDCl$_3$): $\delta_H$=1.31 (m, 2H), 1.32 (m, 3H), 1.34 (s, 3H), 1.58 (m, 1H), 1.59 (m, 1H), 1.74 (m, 1H), 1.77 (s, 3H), 1.79 (m, 2H), 2.17 (m, 1H), 2.29 (s, 6H), 2.32 (m, 1H), 2.42 (t, J=7.5 Hz, 2H), 2.95 (dd, J=13.5, 6.0 Hz, 1H), 3.14 (s, 2H), 3.21 (m, 1H), 3.26 (dd, J=13.5, 10.0 Hz, 1H), 3.86 (m, 1H), 4.18 (m, 1H), 4.66 (m, 1H), 5.16 (ddd, J=10.2, 10.2, 5.5 Hz, 1H), 5.94 (s, 1H), 7.09 (d, J=10.5 Hz, 1H), 7.21 (m, 3H), 7.27 (m, 2H), 7.50 (d, J=10.5 Hz, 1H).

Example 9

Synthesis of cyclo(-L-Am7(methyl)-Aib-L-Phe-D-Pro-)

Compound (Ky-15) of the above formula (3) in which n=3, $X_1$=S and $Y_2$=H.

Cyclo(-L-Ab7-Aib-L-Phe-D-Pro-) (535 mg, 1.0 mmol) was dissolved in DMF (2.0 ml), NaSCH$_3$ (105 mg, 1.5 mmol) was added, and the reaction was allowed to proceed at room temperature for 3 hours. The solvent was distilled off, the residue was extracted with ethyl acetate, and the extract was washed in sequence with a 10% aqueous solution of citric acid, a 4% aqueous solution of sodium hydrogencarbonate and a saturated aqueous solution of sodium chloride. After drying over anhydrous magnesium sulfate, the ethyl acetate was distilled off to give a foam-like solid (362 mg, 72%). HPLC: rt: 7.80 min.

Example 10

Synthesis of cyclo(-L-Am7(2-pyridylmethylthio ether)-Aib-L-Phe-D-Pro-)

Compound (Ky-16) of the above formula (3) in which n=3, $X_1$=S and $Y_2$=2-pyridyl.

Cyclo(-L-Am7(SAc)-Aib-L-Phe-D-Pro-) (265 mg, 0.50 mmol) was dissolved in DMF (2.0 ml), argon gas was passed through the reaction system, 9 M methylamine/methanol (0.27 ml, 2.5 mmol) was added, and the reaction was allowed to proceed for 3 hours. The solvent was distilled off, the residue was again dissolved in DMF (2.0 ml), 2-bromomethylpyridine hydrobromide (190 mg, 0.75 mmol) and triethylamine (0.18 ml, 1.25 mmol) were added, and the reaction was allowed to proceed in an argon atmosphere at room temperature for 3 hours. The solvent was distilled off, the residue was extracted with ethyl acetate, and the extract was treated in the same manner as mentioned above. Purification by silica gel flash chromatography (2% methanol/chloroform) gave an oil (150 mg, 51%). HPLC: rt: 7.54 min. HR-FAB MS (2,2'-dithiodiethanol), 580.2972 [M+H]$^+$, $C_{31}H_{42}N_5O_4S$ (calcd. 580.2958).

Example 11

Synthesis of cyclo(-L-Am7(2-pyridylmethyl,sulfoxide)-Aib-L-Phe-D-Pro-)

Compound (Ky-25) of the above formula (3) in which n=3, $X_1$=SO and $Y_2$=2-pyridylmethyl.

Cyclo(-L-Am7(2-pyridylmethylthio ether)-Aib-L-Phe-D-Pro-) (58.0 mg, 0.10 mmol) was dissolved in DMF (1.0 ml), a 4% aqueous hydrogen peroxide solution (0.13 ml, 0.15 mmol) was added, and the reaction was allowed to proceed for 15 hours. The reaction mixture was extracted with ethyl acetate, the extract was washed with water and dried over anhydrous magnesium sulfate, the ethyl acetate was distilled off, and the residue was purified by silica gel chromatography (2% methanol/chloroform) to give an oil (24.0 mg, 45%). HPLC: rt: 8.21 min. HR-FAB MS (2,2'-dithiodiethanol), 596.2921 [M+H]$^+$, $C_{31}H_{42}N_5O_5S$ (calcd. 596.2907).

Example 12

Synthesis of cyclo(-L-Am7(3-pyridylmethyl)-Aib-L-Phe-D-Pro-)

Compound (Ky-68) of the above formula (3) in which n=3, $X_1$=S and $Y_2$=3-pyridylmethyl.

Cyclo(-L-Am7(SAc)-Aib-L-Phe-D-Pro-) (265 mg, 0.50 mmol) was reacted with 3-bromomethylpyridine hydrobromide (190 mg, 0.75 mmol) in the same manner as in Example 10 to give an oil (167 mg, 58%). HPLC: rt: 8.02 min. HR-FAB MS (2,2'-dithiodiethanol), 580.2939 [M+H]$^+$, $C_{31}H_{42}N_5O_4S$ (calcd. 580.2958).

Example 13

Synthesis of cyclo(-L-Am7(4-pyridylmethyl)-Aib-L-Phe-D-Pro-)

Compound (Ky-26) of the above formula (3) in which n=3, $X_1$=S and $Y_2$=4-pyridylmethyl.

Cyclo(-L-Am7(SAc)-Aib-L-Phe-D-Pro-) (265 mg, 0.50 mmol) was reacted with 4-bromomethylpyridine hydrobromide (190 mg, 0.75 mmol) in the same manner as in Example 10 to give an oil (127 mg, 44%). HPLC: rt: 8.06 min. HR-FAB MS (2,2'-dithiodiethanol), 580.2977 [M+H]$^+$, $C_{31}H_{42}N_5O_4S$ (calcd. 580.2958).

Example 14

Synthesis of cyclo(-L-Am7(benzyl)-Aib-L-Phe-D-Pro-)

Compound (Ky-69) of the above formula (3) in which n=3, $X_1$=S and $Y_2$=phenyl.

Cyclo(-L-Am7(SAc)-Aib-L-Phe-D-Pro-) (265 mg, 0.50 mmol) was reacted with benzyl bromide (128 mg, 0.75 mmol) in the same manner as in Example 10 to give an oil (185 mg, 63%). HPLC: rt: 8.16 min. HR-FAB MS (2,2'-dithiodiethanol), 579.3016 [M+H]$^+$, $C_{32}H_{43}N_4O_4S$ (calcd. 579.3005).

Example 15

Synthesis of cyclo(-L-Am5(1,1,1-trifluoroacetonyl)-Aib-L-Phe-D-Pro-)

Compound (Ky-27) of the above formula (3) in which n=1, $X_1$=S and $Y_2$=COCF$_3$.

Cyclo(-L-Am5(SAc)-Aib-L-Phe-D-Pro-) (251 mg, 0.50 mmol) was reacted with 1,1,1-trifluoro-3-bromoacetone (143 mg, 0.75 mmol) in the same manner as in Example 10 to give an oil (154 mg, 54%). HPLC: rt: 6.83 min. HR-FAB MS (2,2'-dithiodiethanol), 571.2280 [M+H]$^+$, $C_{26}H_{34}F_3O_5N_4S$ (calcd. 571.2202).

Example 16

Synthesis of cyclo(-L-Am6(1,1,1-trifluoroacetonyl)-Aib-L-Phe-D-Pro-)

Compound (Ky-28) of the above formula (3) in which n=2, $X_1$=S and $Y_2$=COCF$_3$.

Cyclo(-L-Am6(SAc)-Aib-L-Phe-D-Pro-) (258 mg, 0.50 mmol) was reacted with 1,1,1-trifluoro-3-bromoacetone (143 mg, 0.75 mmol) in the same manner as in Example 10 to give an oil (134 mg, 47%). HPLC: rt: 7.60 min. HR-FAB MS (2,2'-dithiodiethanol), 585.2391 [M+H]$^+$, $C_{27}H_{36}F_3O_5N_4S$ (calcd. 585.2359).

Example 17

Synthesis of cyclo(-L-Am7(1,1,1-trifluoroacetonyl)-Aib-L-Phe-D-Pro-)

Compound (Ky-29) of the above formula (3) in which n=3, $X_1$=S and $Y_2$=COCF$_3$.

Cyclo(-L-Am7(SAc)-Aib-L-Phe-D-Pro-) (265 mg, 0.50 mmol) was reacted with 1,1,1-trifluoro-3-bromoacetone (143 mg, 0.75 mmol) in the same manner as in Example 10 to give an oil (161 mg, 54%). HPLC: rt: 8.11 min. HR-FAB MS (2,2'-dithiodiethanol), 599.2534 [M+H]$^+$, $C_{28}H_{38}F_3O_5N_4S$ (calcd. 599.2515).

Example 18

Synthesis of cyclo(-L-Am7(1,1,1-trifluoroacetonyl, sulfoxide)-Aib-L-Phe-D-Pro-)

Compound (Ky-71) of the above formula (3) in which n=3, $X_1$=SO and $Y_2$=COCF$_3$.

Cyclo(-L-AM7(1,1,1-trifluoroacetonyl)-Aib-L-Phe-D-Pro-) (90 mg, 0.15 mmol) obtained in Example 17 was oxidized with a 4% aqueous hydrogen peroxide solution in the same manner as in Example 10. An oil (43 mg, 44%) was obtained. HPLC: rt: 8.43 min. HR-FAB MS (2,2'-dithiodiethanol), 615.2450 [M+H]$^+$, $C_{28}H_{38}F_3N_4O_6S$ (calcd. 615.2464).

Example 19

Synthesis of cyclo(-L-Am8(1,1,1-trifluoroacetonyl)-Aib-L-Phe-D-Pro-)

Compound (Ky-73) of the above formula (3) in which n=4, $X_1$=S and $Y_2$=COCF$_3$.

Cyclo(-L-Am8(SAc)-Aib-L-Phe-D-Pro-) (272 mg, 0.50 mmol) was reacted with 1,1,1-trifluoro-3-bromoacetone (143 mg, 0.75 mmol) in the same manner as in Example 10 to give an oil (147 mg, 48%). HPLC: rt: 8.51 min. HR-FAB MS (2,2'-dithiodiethanol), 613.2691 [M+H]$^+$, $C_{29}H_{40}F_3N_4O_5S$ (calcd. 613.2672).

Example 20

Synthesis of cyclo(-L-Am7(acetonyl)-Aib-L-Phe-D-Pro-)

Compound (Ky-72) of the above formula (3) in which n=3, $X_1$=S and $Y_2$=COCH$_3$.

Cyclo(-L-Am7(SAc)-Aib-L-Phe-D-Pro-) (265 mg, 0.50 mmol) was reacted with bromoacetone (102 mg, 0.75 mmol) in the same manner as in Example 10 to give an oil (158 mg, 59%). HPLC: rt: 8.01 min. HR-FAB MS (2,2'-dithiodiethanol), 545.2767 [M+H]$^+$, $C_{28}H_{41}N_4O_5S$ (calcd. 545.2798).

Example 21

Synthesis of cyclo(-L-Am7(acetonyl,sulfoxide)-Aib-L-Phe-D-Pro-)

Compound (Ky-86) of the above formula (3) in which n=3, $X_1$=SO and $Y_2$=COCH$_3$.

Cyclo(-L-Am7(acetonyl)-Aib-L-Phe-D-Pro-) (55 mg, 0.10 mmol) obtained in Example 20 was oxidized with a 4% aqueous hydrogen peroxide solution. An oil (24 mg, 43%) was obtained. HPLC: rt: 4.84 min. HR-FAB MS (2,2'-dithiodiethanol), 561.2846 [M+H]$^+$, $C_{28}H_{41}N_4O_6S$ (calcd. 561.2995).

Example 22

Synthesis of cyclo(-L-Am7(methoxyacetonyl)-Aib-L-Phe-D-Pro-)

Compound (Ky-85) of the above formula (3) in which n=3, $X_1$=S and $Y_2$=COCH$_2$OCH$_3$.

Cyclo(-L-Am7(SAc)-Aib-L-Phe-D-Pro-) (120 mg, 0.23 mmol) obtained in Example 20 was reacted with epibromohydrin (47 mg, 0.35 mmol) to give cyclo(-L-Am7(glycidyl)-Aib-L-Phe-D-Pro-) as an oil (98 mg, 78%). HPLC: rt: 8.05 min. HR-FAB MS (2,2'-dithiodiethanol), 545.2782 [M+H]$^+$, $C_{28}H_{41}O_5N_4S$ (calcd. 545.2798).

Then, the above intermediate was subjected to glycidyl group ring opening with sodium methoxide (0.2 mmol) in methanol; purification by silica gel chromatography gave cyclo(-L-Am7($CH_2CH(OH)OCH_3$)-Aib-L-Phe-D-Pro-) (93 mg, 90%). HPLC: rt: 7.81 min. HR-FAB MS (2,2'-dithiodiethanol), 577.3053 [M+H]$^+$, $C_{29}H_{45}O_6N_4S$ (calcd. 577.3060).

Further, the above compound was treated with the Dess-Martin reagent (271 mg, 0.64 mmol) in anhydrous dichloromethane to give the desired product (69 mg, 72%) as a pale yellow oil. HPLC: rt: 7.52 min. HR-FAB MS (2,2'-dithiodiethanol), 575.2920 [M+H]$^+$, $C_{29}H_{43}O_6N_4S$ (calcd. 575.2903).

Example 23

Synthesis of cyclo(-L-Ah7(acetonyl)-Aib-L-Phe-D-Pro-)

Compound (Ky-74) of the above formula (3) in which n=3, $X_1$=O and $Y_2$=$COCH_3$.

Boc-L-Ah7(allyl)-OH (1.02 g, 1.0 mmol) and H-Aib-L-Phe-D-Pro-OtBu (1.98 g, 4.87 mmol) were subjected to condensation in DMF (10 ml) in the conventional manner of peptide synthesis. Purification by silica gel flash chromatography gave Boc-L-Ah7(allyl)-Aib-L-Phe-D-Pro-OtBu (1.1 g, 35%) as a foam-like substance. HPLC: rt: 9.19 min. MALDI-TOFMS, m/e 710.13 ([M+Na]$^+$). The whole amount thereof was dissolved in TFA (3 ml) on an ice bath and the reaction was allowed to proceed for 4 hours. The TFA was distilled off and ether was added to the residue to give H-L-Ah7(allyl)-Aib-L-Phe-D-Pro-OH-TFA (800 mg, 80%) as a white powder. This was further subjected to cyclization using HATU (967 mg, 2.55 mmol) and DIEA (diisopropylethylamine) (0.84 ml) under high dilution conditions to give cyclo(-L-Ah7(allyl)-Aib-L-Phe-D-Pro-) (314 mg, 49%) as a white solid. HPLC: rt: 6.91 min. MALDI-TOFMS, [M+H]$^+$ 513.75 for $C_{28}H_{40}N_4O_5$ (calcd. 512.64) and [M+Na]$^+$ 535.77 for $C_{28}H_{40}N_4O_5Na$ (calcd. 535.64).

In accordance with Reference Example 3, the allyl group of the above white solid was converted to an epoxide group in anhydrous dichloromethane and the epoxide was purified by silica gel chromatography to give cyclo(-L-Ah7(glycidyl)-Aib-L-Phe-D-Pro-) (150 mg, 47%). HPLC: rt: 5.85 min. MALDI-TOFMS, [M+H]$^+$ 529.76 for $C_{28}H_{40}N_4O_6$ (calcd. 528.64) and [M+Na]$^+$ 551.75 for $C_{28}H_{40}N_4O_5Na$ (calcd. 551.64).

Then, in accordance with Reference Example 4, the epoxy group was reacted with anhydrous LiBr in THF for ring opening to give the bromohydrin form, whereby cyclo(-L-Ah7($CH_2CH(OH)CH_2Br$)-Aib-L-Phe-D-Pro-) (174 mg, 91%) was obtained. HPLC: rt: 5.92 min. MALDI-TOFMS, [M+Li]$^+$ 617.04 for $C_{28}H_{41}BrN_4O_6Li$ (calcd. 616.45) and [M+Na]$^+$ 633.04 for $C_{28}H_{41}BrN_4O_6Na$ (calcd. 633.55).

The cyclic peptide bromohydrin (140 mg, 0.23 mmol) was reacted with the Dess-Martin reagent (292 mg, 0.7 mmol) in anhydrous dichloromethane to give a bromoacetonyl group-containing derivative, namely cyclo(-L-Ah7($CH_2COCH_2Br$)-Aib-L-Phe-D-Pro-) (102 mg, 73%). HPLC: rt: 6.75 min. MALDI-TOFMS, [M+Na]$^+$ 630.61 for $C_{28}H_{39}BrN_4O_6Na$ (calcd. 630.54) and [M+K]$^+$ 646.65 for $C_{28}H_{39}BrN_4O_6K$ (calcd. 646.54).

Further, the bromoacetonyl group was reduced with zinc/acetic acid for conversion thereof to an acetonyl group to give cyclo(-L-Ah7($CH_2COCH_3$)-Aib-L-Phe-D-Pro-) (Ky-74, 37 mg, 48%). HPLC: rt: 6.01 min. MALDI-TOFMS, [M+Na]$^+$ 551.58 for $C_{28}H_{40}N_4O_6Na$ (calcd. 551.64) and [M+K]$^+$ 567.55 for $C_{28}H_{40}N_4O_6K$ (calcd. 567.64).

Example 24

Histone Deacetylase-Inhibiting Activities of Cyclic Tetrapeptides

In this example, Ky-17, 12, 9, 10, 60, 13, 18 and 14 (abbreviations for functional groups: Ae9, Ae9(Bmk), Ae9(Mmk), Ae9(Emk), Ae9(Tfemk), Ae9(Mtmk), Ae9(Actmk) and Ae9(Dmamk)), which have the cyclic tetrapeptide structure containing a carbonyl group in the side chain, Ky-15, 16, 68, 26, 69, 27, 28, 29, 73, 72, 85 and 83, which have the cyclic tetrapeptide structure containing a sulfide bond in the side chain, Ky-25, 71 and 86, which are compounds containing a sulfoxide group, and Ky-74, which is a compound containing an ether bond, were measured for enzyme-inhibiting activity levels.

In carrying out HDAC-inhibiting activity measurements, HDAC solutions were prepared in the following manner. In each 100-mm dish, there were sowed 1×10$^7$ 293T cells and, after 24 hours, they were transfected with a vector (5 µg) expressing human HDAC1 or HDAC4 or murine HDAC6 using the LipofectAmine 2000 reagent (Invitrogen). The human HDAC1 expression vector used was pcDNA3-HD1 (Yang, W. M., Yao, Y. L., Sun, J. M., Davie, J. R. & Seto, E. (1997) J. Biol. Chem. 272, 28001-28007), the human HDAC4 expression vector used was pcDNA3-HD4 (Fischle, W., Emiliani, S., Hendzel, M. J., Nagase, T., Nomura, N., Voelter, W. & Verdin, E. (1999) J. Biol. Chem. 274, 11713-11720), and the murine HDAC6 expression vector used was pcDNA3-mHDA2/HDAC6 (Verdel, A. & Khochbin, S. (1999) J. Biol. Chem. 274, 2440-2445).

After 24 hours of incubation, cells were recovered, washed with PBS, suspended in lysis buffer (50 mM Tris-HCl (pH 7.5), 120 mM NaCl, 5 mM EDTA, 0.5% Nonidet P-40), and sonicated. The supernatant was collected by centrifugation and then deprived of nonspecific proteins using Protein A/G plus agarose beads (Santa Cruz Biotechnologies, Inc.). Thereafter, anti-FLAG M2 antibody (Sigma-Aldrich Inc.) was added, and the reaction was allowed to proceed at 4° C. for 2 hours.

To this were added agarose beads, the reaction was allowed to proceed at 4° C. for 3 hours, and the agarose beads were washed three times with lysis buffer and then once with HD buffer (20 mM Tris-HCl (pH 8.0), 150 mM NaCl, 10% glycerol). The protein bound to the agarose beads was recovered by 1 hour of incubation with FLAG peptide (40 µg) (Sigma-Aldrich Inc.) in HD buffer (200 µl) at 4° C., and the liquid recovered was used, as a reactant solution, in the HDAC-inhibiting activity measurement described below.

HDAC-inhibiting activity evaluation in each in vitro system was made as follows. Each test compound was dissolved in DMSO, a stock solution with a concentration of 10 mM was thus prepared and this was used as an inhibitor stock solution. The assay was carried out by incubating the HDAC solution and a coumarin-labeled acetylated histone peptide solution in the presence of the test compound at 37° C. for 30 minutes (reaction volume 20 µl). To the reaction mixture was added 30 µl of trypsin, and the aminomethylcoumarin released by the enzymatic reaction was assayed using a fluorescent plate reader. In a negative control assay, no inhibitor was added to the reaction system and the same procedure was carried out. The inhibitory activity was expressed in terms of 50% inhibition concentration ("$IC_{50}$ (µM)"). The results thus obtained are shown in Table 1.

Example 25 p21 Promoter Assay of Cyclic Tetrapeptides

As an HDAC-inhibiting activity in an in vivo system, the following measurement was carried out using the p21 promoter inducing activity as an index. MFLL-9 cells used in the experiment are cells stably retaining a fusion gene (Dr. B. Vogelstaein) from the human wild type p21 promoter and luciferase gene. They were cultured using phenol red-free DMEM supplemented with 10% FBS in a steam-saturated incubator at 37° C. in the presence of 5% carbon dioxide. These MFLL-9 cells were sowed onto a 96-well microplate at a cell density of $2 \times 10^4$ cells/well and, after 24 hours of cultivation in 99 µl, per well, of the medium mentioned above, each test compound solution was added, followed by 20 hours of incubation. Here, too, TSA was used as a positive control compound as to the p21 promoter inducing activity resulting from HDAC inhibition activity. In a negative control, the same procedure was carried out without adding any inhibitor to the reaction system.

Using Luciferase Assay Reagent (Promega), the intensity of the luminescence due to the product of the enzymatic reaction involving luciferase expressed within cells was measured. The intensity of the activity of the test compound was expressed in terms of the concentration ("$EC_{1000}$ (µM)") at which the above intensity showed the value of 1000% relative to that of the negative control which was taken as 100%. The results thus obtained are shown in Table 1.

The above results indicated that differences in the structure of the functional group to bind to the central zinc atom in histone deacetylase result in marked differences in the inhibitory activities against the respective enzyme subtypes. The compounds of the invention showed strong inhibitory activity against the respective subtypes. Further, it was shown that the differences in functional group structure result in markedly different levels of inhibitory activity against the respective subtypes and that the compounds of the invention have selectivity against the enzyme subtypes. The selectivity of a compound for the target enzymes can be expected to be modified by readily modifying the structure of the functional group to coordinate with zinc by the method of producing the compound of the present invention.

Example 26

Induction of Excess Acetylation of Histone Proteins by Cyclic Tetrapeptides

In measuring the levels of acetylation of tubulin and histones, each test compound was allowed to act on HeLa cells and the levels of acetylation of tubulin and histones were confirmed by western blotting using anti-acetylated lysine antibodies.

More specifically, human cervical carcinoma cells (HeLa) were cultured using DMEM supplemented with 10% FBS at 37° C. in the presence of 5% carbon dioxide in a water vapor-saturated incubator. These cells were sowed onto a 24-well plate at a cell density of $2.5 \times 10^5$ cells/ml in an amount of 500 µl/well and, after 24 hours of incubation, each test compound solution was added, followed by further 6 hours of incubation. The cells were washed with PBS and mixed with SDS buffer (40 µl), followed by 5 minutes of treatment at 100° C.; the thus-treated sample was electrophoresed on a 5-20% SDS gradient gel, followed by transfer to a membrane film. As for histones, the film was treated with Anti-acetyl-histone H4(Lys8) or Anti-acetyl-histone H3(Lys 9) (Upstate) as a primary antibody and with Anti-rabbit (Amersham) as a secondary antibody and, as for tubulin, the film was treated with Anti-acetylated tubulin (SIGMA) as a primary antibody and Anti-mouse (Amersham) as a secondary antibody and, after treatment with ECL (Amersham Pharmacia Biotech), acetylated band detection was performed. The results thus obtained are shown in FIGS. 1-4.

As shown in FIGS. 1-4, those compounds having potent HDAC-inhibiting activity were confirmed to enhance the acetylation of the histone proteins H3 and H4, and the inhibitory tendency shown was the same as the results ($EC_{1000}$) of p21 promoter inducing activity measurements.

Example 27

Induction of p21 Protein Expression and Inhibition of Apoptosis-Inhibiting Protein Expression by Cyclic Tetrapeptides Levels of expression of intracellular p21, survivin and Bcl-xL proteins were determined by allowing the test compound to act on HeLa cells, followed by western blotting using antibodies reacting with the respective proteins.

More specifically, human cervical carcinoma cells (HeLa) were cultured using DMEM supplemented with 10% FBS at 37° C. in the presence of 5% carbon dioxide in a water vapor-saturated incubator. These cells were sowed onto a 24-well plate at a cell density of $1.5 \times 10^5$ cells/well in an amount of 500 µl/well and, after 24 hours of incubation, each test compound solution was added, followed by further 24 hours of incubation. Here, too, TSA was used as a positive control compound concerning the HDAC-inhibiting activity-due p21 protein expression induction and apoptosis-inhibiting protein expression reduction. In a negative control, the same procedure was carried out without adding any inhibitor to the reaction system.

The cells were washed with PBS and mixed with SDS buffer (40 µl), followed by 5 minutes of treatment at 100° C.; the thus-treated sample was electrophoresed on a 5-20% SDS gradient gel, followed by transfer to a membrane film. As for p21, the film was treated with a primary antibody: Anti-p21 antibody (Santa Cruz Biotechnology) and a secondary antibody: Anti-mouse (Amersham), as for Bcl-xL, the film was treated with a primary antibody: Anti-Bcl-X antibody (PharMingen) and a secondary antibody: Anti-rabbit (Amersham) and, as for survivin, the film was treated with a primary antibody: Anti-survivin antibody (R&D Systems) and a secondary antibody: Anti-rabbit (Amersham) and, after treatment with ECL (Amersham Pharmacia Biotech), p21, Bcl-xL and survivin band detections were performed. The results thus obtained are shown in FIGS. 5 and 6.

Figure 5:
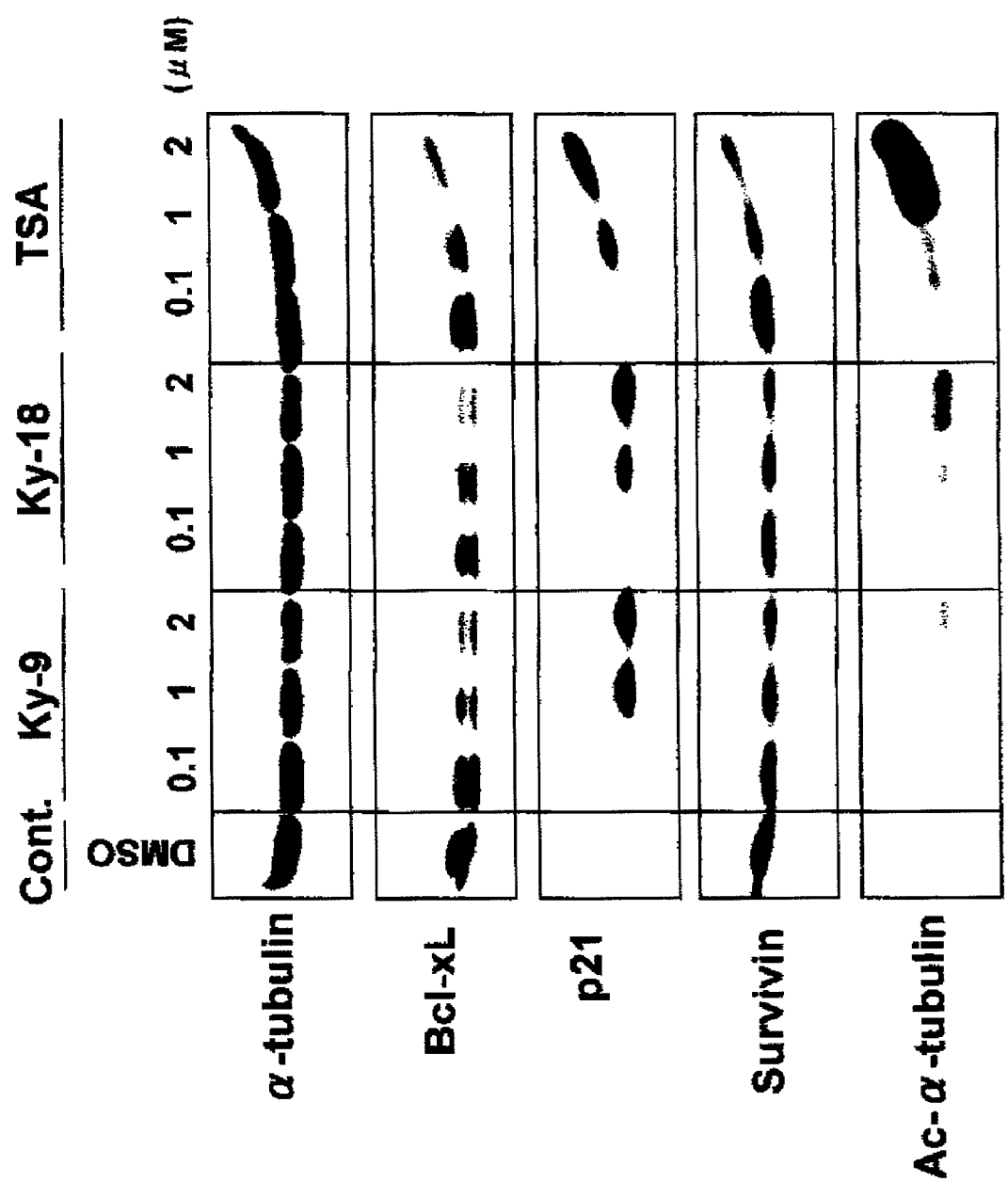
FIG. 5 shows the effects of some compounds according to the invention on the levels of expression of p21, Bcl-xL and survivin.
Figure 6:
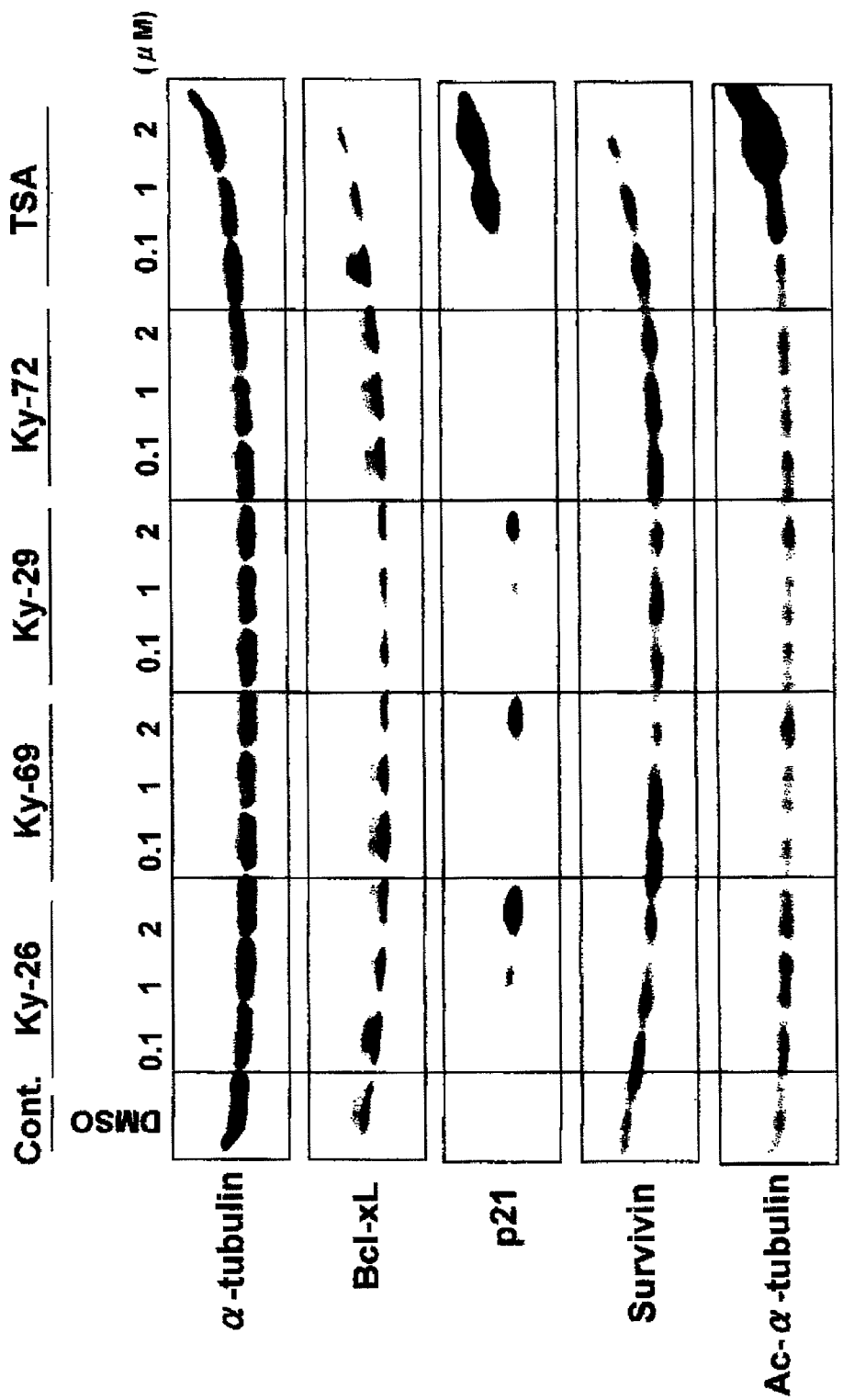
FIG. 6 shows the effects of further several compounds according to the invention on the levels of expression of p21, Bcl-xL and survivin.

As shown in FIGS. 5 and 6, those compounds having potent HDAC-inhibiting activity were confirmed to induce the p21 protein expression. Further, a tendency was shown for the expression of Bcl-xL and survivin to decrease with the increase in inhibitor concentration.

TABLE 1

| Example | Compound | HDAC-inhibiting activity IC$_{50}$ (μM) | | | p21 promoter activity EC$_{1000}$ (μM) |
| --- | --- | --- | --- | --- | --- |
| | | HDAC1 | HDAC4 | HDAC6 | |
| 1 | Ky-17 | >100 | >100 | >100 | >250 |
| 2 | Ky-12 | 0.062 | 0.060 | 0.62 | 0.34 |
| 3 | Ky-9 | 0.038 | 0.028 | >100 | 0.043 |
| 4 | Ky-10 | 0.021 | 0.031 | 8.4 | 0.095 |
| 5 | Ky-60 | 0.37 | 0.46 | >100 | 0.85 |
| 6 | Ky-13 | 0.11 | 0.074 | 40.5 | 0.13 |
| 7 | Ky-18 | 0.11 | 0.19 | 4.3 | 0.013 |
| 8 | Ky-14 | 20 | 17.9 | >100 | 2.4 |
| 9 | Ky-15 | >100 | >100 | >100 | >250 |
| 10 | Ky-16 | 0.023 | 0.011 | 0.058 | 0.20 |
| 11 | Ky-25 | 40.3 | 25.1 | >100 | 1.4 |
| 12 | Ky-68 | 0.40 | 0.33 | 3.7 | 0.20 |
| 13 | Ky-26 | 0.050 | 0.025 | 1.4 | 0.010 |
| 14 | Ky-69 | 0.011 | 0.0065 | 0.12 | 0.041 |
| 15 | Ky-27 | >100 | >100 | >100 | >250 |
| 16 | Ky-28 | 83.0 | 18.4 | >100 | 6.5 |
| 17 | Ky-29 | 1.4 | 0.36 | 35.9 | 0.028 |
| 18 | Ky-71 | >100 | >100 | >100 | 3.4 |
| 19 | Ky-73 | 1.1 | 0.46 | 26.4 | 3.7 |
| 20 | Ky-72 | 1.8 | 1.6 | 19.3 | 0.031 |
| 21 | Ky-86 | 22.2 | 12.8 | >100 | 16.8 |
| 22 | Ky-85 | 0.13 | 0.077 | 1.2 | 0.48 |
| 23 | Ky-74 | >100 | >100 | >100 | >250 |

Example 28

Evaluation of Mechanisms of Action of the Compounds Using a Panel of Human Cancer Cell Lines The characteristics of the human cancer cell proliferation-inhibiting activity of the compounds of the present invention were examined by the "method of evaluating the mechanisms of action of compounds using a panel of human cancer cell lines" as proposed by Yamori et al. (cf. Gan to Kagaku Ryoho (Cancer and Chemotherapy) 29 Suppl. II (2002) and Cancer Chemother. Pharmacol. 52 Suppl. I, S74-79 (2003)).

This system includes 39 human cancer cell lines (7 lung cancer, 6 stomach cancer, 5 colon cancer, 5 ovarian cancer, 6 brain tumor, 5 breast cancer, 2 kidney cancer and 2 prostate cancer cell lines as well as one melanoma line) and the method comprises measuring the in vitro drug susceptibilities of those cancer cell lines and expressing the differences in drug susceptibility among the respective cancer cell lines as a fingerprint. The studies so far made have revealed that drugs similar in chemical structure or in mechanisms of action show fingerprint patterns statistically highly correlated with one another. By utilizing this property, it is possible to estimate the mechanisms of action of a compound. The above method is also characterized in that an anticancer substance showing new and unique mechanisms of action different from those of the existing anticancer agents can be selected.
(Method)

Cancer cells of each cell line are sowed onto a 96-well plate, a sample solution is added on the next day and, after 2 days of cultivation, the cell proliferation is measured by colorimetry using sulforhodamine B. The deviations in effective concentration for the respective cancer cell lines from the mean effective drug concentration for the 39 cancer cell lines subjected to measurement are calculated and shown in the form a fingerprint.
(Results)

A part of the results of evaluation of the effects of the characteristic proliferation-inhibiting activity of the compounds of the invention against human cancer cells as obtained by the above method are described below. The compound (Ky-9) of Example 3 showed potent proliferation-inhibiting activity (50% inhibitory concentration not higher than $10^{-7}$ M) against the lung cancer cell line NCI-H522 and melanoma cell line LOX-IMVI.

The compound (Ky-26) of Example 13 showed especially potent proliferation-inhibiting activity (50% inhibitory concentration not higher than $10^{-8}$ M) against the lung cancer cell line NCI-H522 and showed considerable proliferation-inhibiting effects (50% inhibitory concentration not higher than $10^{-7}$ M) against the breast cancer cell line BSY-1, brain tumor cell lines SF-539 and SNB-75, colon cancer cell lines HCC2998, HT-29 and HCT-116, lung cancer cell lines NCI-H23, NCI-H226, NCI-H460, A549 and DMS114, melanoma cell line LOX-IMVI, ovarian cancer cell lines OVCAR-5 and OVCAR-8, kidney cancer cell line RXF-631L, stomach cancer cell line MKN1 and prostate cancer cell line DU-145.

And, the compound (Ky-72) of Example 20 was found to have especially potent proliferation-inhibiting activity (50% inhibitory concentration not higher than $10^{-8}$ M) against the colon cancer cell line HCT-116 and lung cancer cell line NCI-H522 and show considerable proliferation-inhibiting effects (50% inhibitory concentration not higher than $10^{-7}$ M) broadly against the breast cancer cell line BSY-1, brain tumor cell lines SF-268, SF-295, SF-539 and SNB-75, colon cancer cell lines HCC2998, KM-12 and HT-29, lung cancer cell lines NCI-H23, NCI-H226, NCI-H460, A549 and DMS114, melanoma cell line LOX-IMVI, ovarian cancer cell lines OVCAR-5, OVCAR-8 and SK-OV-3, kidney cancer cell lines RXF-631L and ACHN, stomach cancer cell line MKN1 and prostate cancer cell line DU-145.

The invention claimed is:

1. A compound having histone deacetylase-inhibiting activity, which compound is a side chain carbonyl group-containing cyclic tetrapeptide derivative represented by the general formula (2):

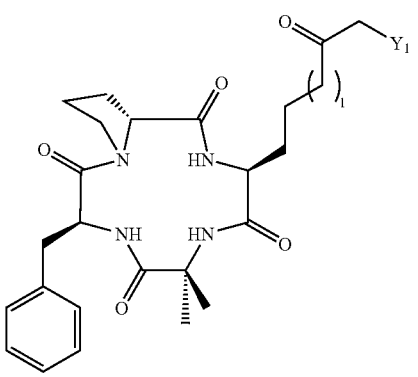

(2)

wherein l represents an integer of 1, 2, 3 or 4 and $Y_1$ represents a —OCH$_3$, —OCH$_2$CH$_3$, —OCH$_2$CF$_3$, —SCH$_3$, —SCOCH$_3$ or —N(CH$_3$)$_2$.

2. A compound having histone deacetylase-inhibiting activity, which compound is a side chain sulfide bond-, sulfoxide group- or ether bond-containing cyclic tetrapeptide derivative represented by the general formula (3):

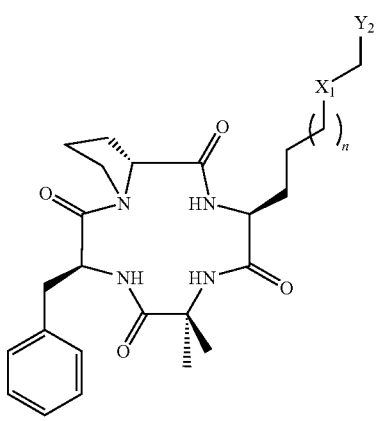

(3)

wherein n represents an integer of 1, 2, 3 or 4 and $X_1$ represents —S—, —SO— or —O— and $Y_2$ represents a hydrogen atom, —COCF$_3$, —COCH$_3$, —COCH$_2$OCH$_3$, a phenyl group or 2-, 3- or 4-pyridyl group, with the proviso that when $X_1$ is S, $Y_2$ is not COCF$_3$.

3. A pharmaceutical composition which comprises, as an active ingredient, the cyclic tetrapeptide derivative according to claim 1 or a pharmaceutically acceptable salt thereof.

4. A compound having histone deacetylase-inhibiting activity which is a side chain sulfide bond-containing cyclic tetrapeptide derivative represented by the general formula (9):

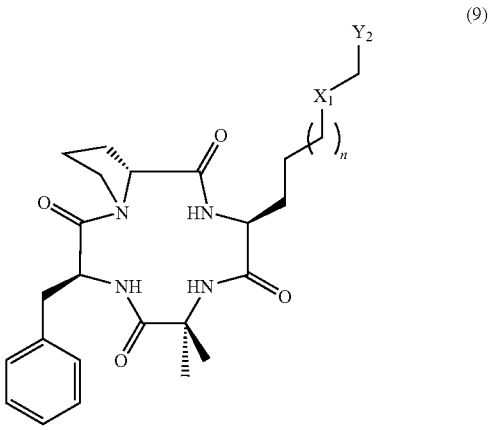

(9)

wherein n represents an integer of 1, 2, 3 or 4, $X_1$ represents —S— and $Y_2$ represents a phenyl group or a 2-, 3- or 4-pyridyl group.

5. A pharmaceutical composition which comprises, as an active ingredient, the cyclic tetrapeptide derivative according to claim 4 or a pharmaceutically acceptable salt thereof.

6. A pharmaceutical composition which comprises, as an active ingredient, the cyclic tetrapeptide derivative according to claim 2 or a pharmaceutically acceptable salt thereof.

* * * * *